US011090374B2

(12) United States Patent
He et al.

(10) Patent No.: US 11,090,374 B2
(45) Date of Patent: Aug. 17, 2021

(54) **ENHANCING IMMUNOGENICITY OF *STREPTOCOCCUS PNEUMONIAE* POLYSACCHARIDE-PROTEIN CONJUGATES**

(71) Applicant: Merck Sharp & Dohme Corp., Rahway, NJ (US)

(72) Inventors: Jian He, Blue Bell, PA (US); John E. MacNair, Lansdale, PA (US); William J. Smith, Harleysville, PA (US); Michael A. Winters, Doylestown, PA (US); Joseph G. Joyce, Lansdale, PA (US); Chitrananda Abeygunawardana, Ambler, PA (US); Luwy Musey, Blue Bell, PA (US); Hari Pujar, Berwyn, PA (US); Julie M. Skinner, Phoenixville, PA (US); Emily Wen, Harleysville, PA (US); Patrick McHugh, Pipersville, PA (US); John Michael Williams, Hillsborough, NJ (US); Catherine Lancaster, Southhampton, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/487,550

(22) PCT Filed: Feb. 20, 2018

(86) PCT No.: PCT/US2018/018729
§ 371 (c)(1),
(2) Date: Aug. 21, 2019

(87) PCT Pub. No.: WO2018/156491
PCT Pub. Date: Aug. 30, 2018

(65) Prior Publication Data
US 2020/0054733 A1 Feb. 20, 2020

Related U.S. Application Data

(60) Provisional application No. 62/555,444, filed on Sep. 7, 2017, provisional application No. 62/463,216, filed on Feb. 24, 2017.

(51) Int. Cl.
*A61K 39/09* (2006.01)
*A61K 47/64* (2017.01)
*A61P 31/04* (2006.01)
*A61K 39/116* (2006.01)
*A61K 39/00* (2006.01)

(52) U.S. Cl.
CPC .......... *A61K 39/092* (2013.01); *A61K 39/116* (2013.01); *A61K 47/646* (2017.08); *A61P 31/04* (2018.01); *A61K 2039/6037* (2013.01)

(58) Field of Classification Search
None
See application file for complete search history.

(56) References Cited

U.S. PATENT DOCUMENTS

| 8,192,746 B2 | 6/2012 | Caulfield et al. |
| 8,808,707 B1 | 8/2014 | Siber |
| 9,669,084 B2 | 6/2017 | Siber |
| 10,406,220 B2 | 9/2019 | Siber et al. |
| 2006/0263390 A1 | 11/2006 | Giannozzi et al. |
| 2015/0202309 A1 | 7/2015 | Emini et al. |
| 2017/0021006 A1 | 1/2017 | Watson et al. |

FOREIGN PATENT DOCUMENTS

| EP | 2932980 A1 | 10/2015 |
| EP | 2865392 B2 | 2/2020 |
| WO | 2006110352 A2 | 10/2006 |
| WO | 2006110381 A1 | 10/2006 |
| WO | 2007127665 A2 | 11/2007 |
| WO | 2008045852 A2 | 4/2008 |
| WO | 2008079653 A1 | 7/2008 |
| WO | 2008079732 A2 | 7/2008 |
| WO | 2008118752 A2 | 10/2008 |
| WO | 2008143709 A2 | 11/2008 |
| WO | 2009009629 A1 | 1/2009 |
| WO | 2010080484 A1 | 7/2010 |
| WO | 2010080486 A2 | 7/2010 |
| WO | 2011041003 A2 | 4/2011 |
| WO | 2011100151 A1 | 8/2011 |

(Continued)

OTHER PUBLICATIONS

Caro-Aguilar, Ivette et al., Immunogenicity differences of a 15-valent pneumococcal polysaccharide conjugate vaccine (PCV15) based on vaccine dose, route of immunization and mouse strain, Vaccine, 2017, 865-872, 35(6).

(Continued)

*Primary Examiner* — Brian Gangle
(74) *Attorney, Agent, or Firm* — Matthew A. Leff; John C. Todaro

(57) ABSTRACT

The present invention provides immunogenic compositions having one or more polysaccharide-protein conjugates in which one or more polysaccharides from *Streptococcus pneumoniae* bacterial capsules are conjugated to a carrier protein in an aprotic solvent such as dimethylsulfoxide (DMSO). The present invention also provides methods for providing an enhanced immune response to a pneumococcal polysaccharide protein conjugate vaccine comprising administering to a human subject an immunogenic composition comprising polysaccharide-protein conjugates prepared in DMSO conditions.

14 Claims, 3 Drawing Sheets
Specification includes a Sequence Listing.

(56) References Cited

FOREIGN PATENT DOCUMENTS

| | | |
|---|---|---|
| WO | 2011151760 A2 | 12/2011 |
| WO | 2012078482 A1 | 6/2012 |
| WO | 2014097099 A2 | 6/2014 |
| WO | 2015110940 A2 | 7/2015 |
| WO | 2015110941 A2 | 7/2015 |
| WO | 2015110942 A2 | 7/2015 |
| WO | WO2016020499 | 2/2016 |
| WO | 2016113644 A1 | 7/2016 |
| WO | 2016178123 A1 | 11/2016 |
| WO | 2017013548 A1 | 1/2017 |
| WO | 2017085586 A1 | 5/2017 |
| WO | 2017085602 A1 | 5/2017 |
| WO | 2018027126 A1 | 2/2018 |
| WO | 2018126229 A2 | 7/2018 |
| WO | 2018134693 A1 | 7/2018 |
| WO | 2018144438 A1 | 8/2018 |
| WO | 2018144439 A1 | 8/2018 |
| WO | 2018156465 A1 | 8/2018 |
| WO | 2018156467 A1 | 8/2018 |
| WO | 2018156468 A1 | 8/2018 |
| WO | 2019036313 A1 | 2/2019 |
| WO | 2019050813 A1 | 3/2019 |
| WO | 2019050814 A1 | 3/2019 |
| WO | 2019050815 A1 | 3/2019 |
| WO | 2019050816 A1 | 3/2019 |
| WO | 2019050818 | 3/2019 |
| WO | 2019083865 A1 | 5/2019 |
| WO | 2019139692 A2 | 7/2019 |
| WO | 2019212842 A1 | 11/2019 |
| WO | 2019212844 A1 | 11/2019 |
| WO | 2019212846 A1 | 11/2019 |
| WO | 2019236435 A1 | 12/2019 |
| WO | 2020121159 A1 | 6/2020 |
| WO | 2020131763 A2 | 6/2020 |
| WO | 2020208502 A1 | 10/2020 |
| WO | 2020247299 A1 | 12/2020 |
| WO | 2020247301 A1 | 12/2020 |

OTHER PUBLICATIONS

Skinner et al., Pre-clinical Evaluation of a 15-Valent Pneumococcal Conjugate Vaccine (PCV15-CRM197) in an Infant-Rhesus Monkey Immunogenicity Model, Vaccine, 2011, 8870-8876, 29.

ENHANCING IMMUNOGENICITY OF
STREPTOCOCCUS PNEUMONIAE
POLYSACCHARIDE-PROTEIN
CONJUGATES

FIELD OF INVENTION

The present invention provides immunogenic compositions comprising at least one Streptococcus pneumoniae polysaccharide conjugated to $CRM_{197}$ using reductive amination in an aprotic solvent such as dimethylsulfoxide (DMSO). The invention also provides methods for enhancing immunogenicity of immunogenic compositions having one or more polysaccharide-protein conjugates in which one or more polysaccharides from S. pneumoniae bacterial capsules are conjugated to a carrier protein using reductive amination performed in an aprotic solvent such as DMSO.

BACKGROUND OF THE INVENTION

Streptococcus pneumoniae is a Gram-positive bacterium and the most common cause of invasive bacterial disease (such as pneumonia, bacteraemia and meningitis and Otitis media) in infants and young children. Pneumococcus is encapsulated with a chemically linked polysaccharide which confers serotype specificity. There are over 90 known serotypes of pneumococci, and the capsule is the principle virulence determinant for pneumococci, as the capsule not only protects the inner surface of the bacteria from complement, but is itself poorly immunogenic. Polysaccharides are T-cell independent antigens, and can not be processed or presented on MHC molecules to interact with T-cells. They can however, stimulate the immune system through an alternate mechanism which involves cross-linking of surface receptors on B cells.

Children less than 2 years of age do not mount an immune response to most polysaccharide vaccines, so it has been necessary to render the polysaccharides immunogenic by chemical conjugation to a protein carrier. Coupling the polysaccharide, a T-cell independent antigen, to a protein, a T-cell dependent antigen, confers upon the polysaccharide the properties of T cell dependency including isotype switching, affinity maturation, and memory induction.

There are many conjugation reactions that have been employed for covalently linking polysaccharides to proteins. Three of the more commonly employed methods include: 1) reductive amination, wherein the aldehyde or ketone group on one component of the reaction reacts with the amino or hydrazide group on the other component, and the C=N double bond formed is subsequently reduced to C—N single bond by a reducing agent; 2) cyanylation conjugation, wherein the polysaccharide is activated either by cyanogen bromide (CNBr) or by 1-cyano-4-dimethylamrnoniumpyridinium tetrafluoroborate (CDAP) to introduce a cyanate group to the hydroxyl group, which forms a covalent bond to the amino or hydrazide group upon addition of the protein component; and 3) a carbodiimide reaction, wherein carbodiimide activates the carboxyl group on one component of the conjugation reaction, and the activated carbonyl group reacts with the amino or hydrazide group on the other component. These reactions are also frequently employed to activate the components of the conjugate prior to the conjugation reaction.

Reductive amination has been utilized to conjugate S. pneumoniae polysaccharides. See, for example, U.S. Pat. No. 8,192,746, U.S. Patent Application Publication No. 20170021006 and International Patent Application Publication Nos. WO2011/110381 and WO2015/110941. Reductive amination involves two steps: (1) oxidation of the antigen, and (2) reduction of the antigen and a carrier protein to form a conjugate. The reduction step can take place in an aqueous solvent or an aprotic solvent such as DMSO. See, e.g., International Patent Application Publication No. WO2016/113644.

SUMMARY OF THE INVENTION

The present invention provides immunogenic compositions comprising polysaccharides from one or more of S. pneumoniae serotypes 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, and 38 conjugated to a carrier protein, wherein the conjugation reaction whereby the polysaccharide is conjugated to the carrier protein is in an aprotic solvent. In one embodiment, for compositions having identical serotypes, one or more of the serotypes prepared in an aprotic solvent have increased immunogenicity when compared to the same one or more serotypes prepared under aqueous conditions.

The present invention provides immunogenic compositions comprising polysaccharide protein conjugates prepared from one or more of S. pneumoniae serotypes 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, and 38 conjugated to a carrier protein, wherein the polysaccharide protein conjugates are made by a process comprising the step of conjugating the polysaccharide to the carrier protein in an aprotic solvent.

The invention also provides methods of conjugating a polysaccharide from S. pneumoniae serotype 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, or 38 to a carrier protein, comprising the step of conjugating the polysaccharide to the carrier protein in an aprotic solvent.

The invention also provides methods of treating a subject with an immunogenic composition comprising one or more polysaccharides from S. pneumoniae serotypes 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, or 38 conjugated to a carrier protein, wherein the polysaccharide is conjugated to the carrier protein in an aprotic solvent.

In certain embodiments, polysaccharides from one or more of S. pneumoniae serotypes 1, 3, 4, 5, 9V, 11A, 12F, and 14 are conjugated to a carrier protein in an aprotic solvent. In certain embodiments, polysaccharides from one or more of S. pneumoniae serotypes 2, 6C, 6D, 7B, 7C, 8, 9N, 15A, 15C, 16F, 17F, 20, 21, 22A, 23A, 23B, 24F, 27, 28A, 31, 34, 35A, 35B, 35F, and 38 are conjugated to a carrier protein in an aprotic solvent.

In certain embodiments, polysaccharides from one or more of S. pneumoniae serotypes 3 and 18C are conjugated to a carrier protein in an aprotic solvent. In one aspect of this embodiment, polysaccharides from S. pneumoniae serotype 3 are conjugated to a carrier protein in an aprotic solvent. In one aspect of this embodiment, polysaccharides from S. pneumoniae serotype 18C are conjugated to a carrier protein in an aprotic solvent.

In certain embodiments, the conjugation reaction used to conjugate polysaccharide to the carrier protein is reductive amination.

In certain embodiments, the aprotic solvent is DMSO.

In certain embodiments, the carrier protein is $CRM_{197}$.

In certain embodiments, conjugates prepared in DMSO have a lysine loss value greater than 5.0. In one aspect, conjugates prepared in DMSO have a lysine loss value between 7.0 and 18.0 inclusive.

In certain embodiments, the immunogenic composition further comprises polysaccharides from one or more of S. pneumoniae serotypes 6A, 6B, 7F, 10A, 15B, 19A, 19F, 22F, 23F, and 33F conjugated to a carrier protein, wherein the conjugation reaction whereby the polysaccharide is conjugated to the carrier protein is in an aprotic solvent. In certain aspects of this embodiment, the conjugation reaction is reductive amination. In certain aspects, the aprotic solvent is DMSO. In certain aspects, the carrier protein is $CRM_{197}$. In one aspect, the immunogenic compostion comprises polysaccharide from S. pneumoniae serotypes 6A, 6B, 7F, 18C, 19A, 19F, and 23F conjugated to a carrier protein, wherein the conjugation reaction whereby the polysaccharide from S. pneumoniae serotypes 6A, 6B, 7F, 18C, 19A, 19F, or 23F is conjugated to the carrier protein is in an aprotic solvent. In certain aspects, the polysaccharide is from S. pneumoniae serotypes 18C, 19A, 19F or 23F.

In certain embodiments, the immunogenic compositions of the invention further comprises polysaccharides from one or more of S. pneumoniae serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 conjugated to a carrier protein, wherein the conjugation reaction whereby the polysaccharide from S. pneumoniae serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, or 38 is conjugated to the carrier protein is in an aqueous solvent. In one aspect, between 35-100% of the serotypes in the immunogenic composition are prepared using reductive amination under DMSO conditions and the remaining polysaccharide protein conjugates are prepared under aqueous conditions.

In one specific embodiment, the invention provides an immunogenic composition consisting essentially of polysaccharides from S. pneumoniae serotypes 1, 3, 4, 5, 6A, 6B, 7F, 9V, 14, 18C, 19A, 19F, 22F, 23F and 33F conjugated to $CRM_{197}$ polysaccharide, wherein the conjugation reaction for S. pneumoniae serotypes 6A, 6B, 7F, 18C, 19A, 19F, and 23F is in DMSO conditions and the conjugation reaction for S. pneumoniae serotypes 1, 3, 4, 5, 9V, 14, 22F and 33F is in an aqueous solvent, and optionally further comprising about 0.2% w/v PS-20.

The present invention also provides methods for inducing a protective immune response in a human subject comprising administering any of the immunogenic compositions of the invention. In certain embodiments, the subject is 50 years or older and/or immunocompromised. In certain embodiments, the subject is 2 years old or younger. In certain embodiments, the subject is immunocompromised.

The present invention also provides methods for providing an enhanced immune response to a pneumococcal polysaccharide (PnPs) protein conjugate vaccine comprising administering to a animal subject an immunogenic composition comprising polysaccharide-protein conjugates comprising S. pneumoniae capsular polysaccharides from a first set of two or more pneumococcal serotypes conjugated to one or more carrier proteins, wherein the two or more of the polysaccharide-protein conjugates from the first set are prepared using reductive amination under DMSO conditions. In one embodiment, said enhanced immune response is relative to a control animal receiving an immunogenic composition wherein one or more of the two or more polysaccharide-protein conjugates from the first set are prepared using reductive amination in aqueous conditions. In one embodiment, the control animal is a mouse. In another embodiment, the control animal is a human. In certain embodiments, the methods employ pneumococcal polysaccharide protein conjugate vaccine which comprises additional polysaccharide-protein conjugates comprising S. pneumoniae capsular polysaccharides from a second set of pneumococcal serotypes conjugated to one or more carrier proteins are prepared using reductive amination under aqueous conditions, wherein serotypes from the second set are different from serotypes in the first set.

In certain embodiments, the methods employ pneumococcal polysaccharide protein conjugate vaccine where the pneumococcal serotypes are selected from serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 33F, 34, 35A, 35B, 35F, and 38.

In certain embodiments, the methods employ pneumococcal polysaccharide protein conjugate vaccine where polysaccharide-protein conjugates from serotype 3 or 18C are prepared using reductive amination under DMSO conditions.

In certain embodiments, the methods employ pneumococcal polysaccharide protein conjugate vaccine where the polysaccharide-protein conjugates from the first set of pneumococcal serotypes are selected from serotypes 6A, 6B, 7F, 18C, 19A, 19F, and 23F.

In certain embodiments, the methods employ pneumococcal polysaccharide protein conjugate vaccine where polysaccharide-protein conjugates from the first set of pneumococcal serotypes comprise serotypes 6A, 6B, 7F, 18C, 19A, 19F, and 23F, which are prepared using reductive amination under DMSO conditions, and polysaccharide-protein conjugates from a second set of serotypes are prepared under aqueous conditions.

In one specific embodiment, the methods employ pneumococcal polysaccharide protein conjugate vaccine where polysaccharide-protein conjugates from serotypes 6A, 6B, 7F, 18C, 19A, 19F, and 23F are prepared using reductive amination under DMSO conditions and polysaccharide protein conjugates from serotypes 1, 3, 4, 5, 9V, 14, 22F and 33F are prepared under aqueous conditions.

In certain embodiments, the methods employ pneumococcal polysaccharide protein conjugate vaccine where polysaccharide protein conjugates from between 35-100% of the serotypes are prepared using reductive amination under DMSO conditions and the remaining polysaccharide protein conjugates are prepared under aqueous conditions. In one aspect, polysaccharide protein conjugates from between 45-80% of the serotypes are prepared using reductive amination under DMSO conditions and the remaining polysaccharide protein conjugates are prepared under aqueous conditions. In another aspect, polysaccharide protein conjugates from between 75-100% of the serotypes are prepared using reductive amination under DMSO conditions and the remaining polysaccharide protein conjugates are prepared under aqueous conditions.

In certain embodiments, the methods employ pneumococcal polysaccharide protein conjugate vaccine where the carrier protein is selected from the group consisting of Neisseria meningitides Outer Membrane Protein Complex (OMPC), tetanus toxoid, diphtheria toxoid, protein D and $CRM_{197}$. In one aspect, the carrier protein is $CRM_{197}$.

In certain embodiments, the methods employ pneumococcal polysaccharide protein conjugate vaccine where the conjugates prepared using reductive amination under DMSO conditions have a higher proportion of glycopeptide bonds formed as measured by protein lysine loss value greater than 5.0. In one aspect of this embodiment, the conjugates prepared using reductive amination under DMSO conditions have a lysine loss value between 7.0 to 18 inclusive. In another aspect, the conjugates prepared using reductive amination under DMSO conditions have a lysine loss value greater than 9.0, 9.1, 9.2, 9.3, 9.4, 9.5, or 10.0.

In another specific embodiment, the invention provides a method for providing an enhanced immune response to a pneumococcal polysaccharide (PnPs) protein conjugate vaccine consisting essentially of polysaccharides from *S. pneumonia* serotypes 1, 3, 4, 5, 6A, 6B, 7F, 9V, 14, 18C, 19A, 19F, 22F, 23F and 33F conjugated to $CRM_{197}$ polysaccharide, wherein the method comprises administering to a human subject an immunogenic composition comprising polysaccharide-protein conjugates from a first set and a second set of pneumococcal serotypes, wherein the first set of serotypes consists of 6A, 6B, 7F, 18C, 19A, 19F, and 23F and are prepared using reductive amination under DMSO conditions, and the second set of serotypes consists of 1, 3, 4, 5, 9V, 14, 22F and 33F and are prepared under aqueous conditions.

In certain embodiments, the enhanced immune response in animals vaccinated with immunogenic compositions produced by the methods of the invention is measured by serum IgG or opsonophagocytic antibody Geometric Mean Titers. In one aspect, the enhanced immune response to a pneumococcal serotype is 10% or greater compared to polysaccharide-protein conjugate from the same pneumococcal serotype prepared under aqueous conditions. In one embodiment, the animal is a mouse. In another embodiment, the animal is a human.

In certain embodiments, the methods are employed with a human subject which is 50 years old or older. In certain embodiments, the methods are employed with a human subject which is 2 years old or younger. In certain embodiments, the methods are employed with a human subject which is immunocompromised.

The invention also provides methods of preparing a pneumococcal polysaccharide-protein conjugate by reductive amination, the method comprising:

a) reacting a *Streptococcus pneumoniae* polysaccharide selected from serotypes 3, 6A, 6B, 7F, 9V, 14, 18C, 19A, 19F, 22F, 23F, and 33F with an amount of an oxidant (e.g., a periodate) to form an activated polysaccharide having an activation level from 0.05 to 0.22;

b) reacting the activated polysaccharide with a carrier protein in an aprotic solvent, optionally in the presence of a reducing agent, to form a polysaccharide-protein conjugate;

wherein the conjugate has a lysine loss value between 7.0 to 18.0 inclusive.

In certain embodiments, the activation level is from 0.09 to 0.22.

In certain embodiments, the oxidant is periodate.

In certain embodiments, the activation level is measured by derivitizing aldehydes on the polysaccharide with thiosemicarbazide.

In certain embodiments, the reducing agent is a cyanoborohydride salt such as sodium cyanoborohydride.

In certain embodiments, the carrier protein is selected from the group consisting of tetanus toxoid, diphtheria toxoid, and $CRM_{197}$. In one embodiment, the carrier protein is $CRM_{197}$.

The present invention also provides a quantitative method for determining the aldehyde level (i.e., the level of periodate activation) in an activated polysaccharide comprising the steps of:

a) derivatizing the activated polysaccharide to form a derivatized polysaccharide by reacting with a derivatizing agent until completion (i.e., the reaction plateaus);

b) isolating the derivatized polysaccharide by high performance size exclusion chromatography (to remove unreacted derivatizing agent and matrix components);

c) quantifying the UV absorbance of the derivatized polysaccharide.

The derivatizing agent may be selected from the group consisting of thiosemicarbazide, thiosemicarbazide structural analogs, hydrazides, hydrazine, semicarbazide, semicarbazide structural analogs, aminooxy compounds or aromatic amines.

In one embodiment, the quantifying in step c) is by comparison to a derivative standard. In one embodiment, the quantifying in step c) is by measurement against predetermined extinction coefficient.

DETAILED DESCRIPTION OF THE INVENTION

Figure 1:
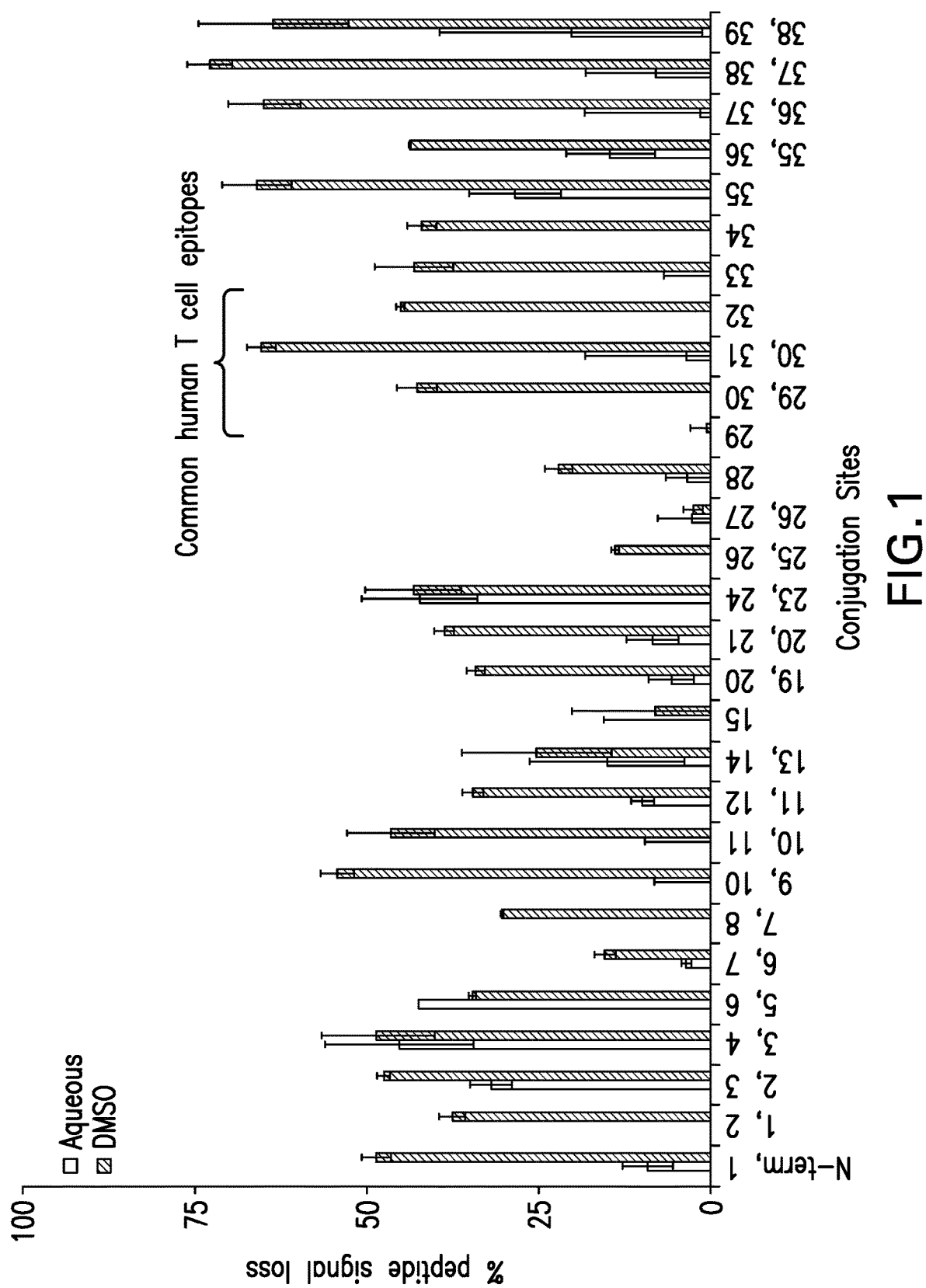
FIG. 1. Extent of conjugation at different lysine sites on $CRM_{197}$ as determined by tryptic peptide mapping. Serotype 19A Ps-$CRM_{197}$ conjugates, prepared by reductive amination in either aqueous solution or DMSO, were digested by trypsin and analyzed by LC-UV-MS. The loss of peptide signal compared to $CRM_{197}$ control samples was plotted against the sites of conjugation.

The present invention provides immunogenic compositions comprising pneumococcal polysaccharide-protein conjugates, in which conjugates from at least one pneumococcal serotype are prepared using reductive amination in an aprotic solvent such as DMSO. The present invention is based, in part, on the discovery that the use of DMSO as a solvent during reductive amination of polysaccharide-protein conjugates results in the unexpectedly superior stability and enhanced immunogenicity for those serotypes relative to the same conjugates prepared under aqueous conditions. The present invention relates to the advantages of DMSO solvent in enhancing the covalent associations of polysaccharide to protein through direct consumption of lysine residues on the surface of the carrier protein. For most serotypes tested, a "lysine loss" that provided good immunogenicity (≥7.0) could be achieved at a lower polysaccharide activation level (0.05 to 0.22) through conjugation in an aprotic solvent than in an aqueous buffer. The increased covalent association has a direct benefit to increasing the stability of the polysaccharide protein conjugate and in enhancing the immune response to those particular polysaccharide antigens conjugated in DMSO.

Without being bound by any theory, one possible mechanism for the enhanced immunogenicity observed with glycoconjugates prepared in DMSO include an increased number of linkages between the carbohydrate (capsular polysaccharide) and lysine residues on the surface of the carrier protein which would result in additional attachment points between the protein and polysaccharide to impart stability and counter chemical depolymerization or breakdown of the peptide carbohydrate bond. See, e.g., Hsieh, Characterization of Saccharide-$CRM_{197}$ Conjugate Vaccines in Brown F, Corbel M, Griffiths E (eds): Physico-Chemical Procedures for the Characterization of Vaccines. Dev. Biol. Basel, Karger, 2000, vol 103, pp. 93-104. An additional benefit of the increased polysaccharide-protein linkages that are created during conjugation in the DMSO solvent could be additional opportunities for successful presentation of peptide-carbohydrate to T-cells. It can be appreciated that due to the genetic varability in the human population resulting in varying abilities and sensitivity of loading or associating with specific peptide sequences conjugated to carbohydrate antigens, that additional points of attachment on the carrier protein would allow for increased chances for successful antigen presentation at the surface of an APC to allow for a T-cell dependent response to an otherwise T-cell independent antigen. Another possible mecahnsim of enhanced immunogenicity observed by conjugation in the DMSO solvent could be due to the denaturation of $CRM_{197}$ in organic solvent, which exposes additional lysines for polysaccharide linkages giving increased chances for glycopeptide presentation at the surface of an APC for T-cell dependent response to different peptide epitopes. See Avci et al., 2011, Nature Medicine 17: 1602-1610.

Yet another benefit of conjugation in an organic solvent generating denatured $CRM_{197}$ in the conjugates could be reduced immunological interference of antibodies against native $CRM_{197}$ epitopes. A further benefit of the increased polysaccharide-protein linkages that are created during conjugation in the DMSO solvent could be the formation of larger sized polysaccharide protein conjugates resulting in enhanced immunogenicity. The compositions of the invention are believed to provide significant advantages in eliciting a human response.

As shown in the Example 5, a polysaccharide protein conjugate prepared from *S. pneumoniae* serotype 3 using reductive amination in DMSO showed increased immunogenicity (compared to the same conjugate prepared using reductive amination in water) in a mouse model as measured by opsophagocytic activity (OPA). Moreover, as shown in the Example 6, a 15-valent pneumococcal conjugate vaccine having seven serotypes prepared using reductive amination in DMSO (and the other eight prepared in an aqueous solvent) tended to show superior immunogenicity in humans (with 4 serotypes superior with statistical significance) for all seven serotypes prepared in DMSO compared to the corresponding 15-valent PCV where all 15 seroytpes were prepared in an aqueous solvent.

As shown in Example 4, plotting the peptide signal decrease for lysine locations on the $CRM_{197}$ protein in serotype 19A conjugates against possible sites of conjugation (compared to a CRM197 control) uncovered additional conjugation sites located in previously identified common human T-cell peptide epitopes (See Raju et al., 1995, Eur. J. Immunol. 25:3207-3214, located in peptide 411-430 and peptide 431-450 of $CRM_{197}$ sequence). Accordingly, in certain embodiments, the present invention is also directed to immunogenic compositions comprising one or more polysaccharide-$CRM_{197}$ conjugates, wherein at least one of the polysaccharide-$CRM_{197}$ conjugates is prepared in an aprotic solvent and wherein a conjugate prepared in an aprotic solvent demonstrates greater accessibility of lysines residues within amino acids 411-430 or 431-450 of $CRM_{197}$ compared to the same conjugate prepared in an aqeuous solvent. In certain embodiments, the present invention is also directed to immunogenic compositions comprising one or more polysaccharide-$CRM_{197}$ conjugates, wherein at least one of the polysaccharide-$CRM_{197}$ conjugates is prepared in an aprotic solvent and wherein one or more lysine residues within amino acids 411-430 or 431-450 of $CRM_{197}$ in a conjugate prepared in an aprotic solvent are conjugated more than 10%. In certain embodiments, the present invention is directed to methods for increasing the accessibility of lysine residues within $CRM_{197}$, particularly within amino acids 411-430 or 431-450 of $CRM_{197}$, comprising conjugating a polysaccharide to $CRM_{197}$ in an aprotic solvent. In certain aspects of this embodiment, one or more lysine residues within amino acids 411-430 or 431-450 of $CRM_{197}$ in a conjugate prepared in an aprotic solvent are conjugated more than 10%. In these embodiments, the polysaccharide can be from any organism suitable for preparing an immunogenic composition. In certain aspects, the polysaccharide is from *N. meningitides* or *S. pneumoniae*. The polysaccharide may be from any serotype of these organisms.

As used herein, the terms "aqueous solvent" or "aqueous conditions" when used with conjugation, such as reductive amination, refers use of water as the solvent for the conjugation reaction. The water may contain buffers and other components except that no organic solvent is present.

As used herein, the terms "aprotic solvent", when used with conjugation, such as reductive amination, refers use of a polar aprotic solvent, or a combination of polar aprotic solvents, as the solvent for the conjugation reaction. Examples of polar aprotic solvents include, but are not limited to, dimethylsulfoxide (DMSO), dimethylformamide (DMF), and hexamethylphosphoramide (HMPA). The aprotic solvent may have some water present, for example, up to 1%, 2%, 5%, 10% or 20%.

As used herein, "DMSO solvent" and "DMSO conditions" are used interchangeably.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular *S. pneumoniae* polysaccharide protein conjugates and no other *S. pneumoniae* polysaccharide protein conjugates from a different serotype.

As used herein, "lysine loss" refers to the lysine consumption during conjugation and is determined by the difference between the average measured amount of lysine in the conjugate and the expected amount of lysine in the starting protein. Example 4 describes one method for determining "lysine loss".

As used herein, the term "polysaccharide" is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like.

When referring to percentages of serotypes in the immunogenic composition being prepared under in an aprotic solvent (e.g., DMSO) and the remaining polysaccharide protein conjugates being prepared under aqueous conditions, it is meant to simply refer to the number of serotypes prepared in an aprotic solvent divided by the total number of serotypes in the composition.

As used herein, all ranges, for example, pH, temperature, and concentrations, are meant to be inclusive. For example, a pH range from 5.0 to 9.0 is meant to include a pH of 5.0 and a pH of 9.0. Similarly, a temperature range from 4 to 25° C. is meant to include the outer limits of the range, i.e., 4° C. and 25° C.

Polysaccharide

*S. pneumonia* capsular polysaccharides that can be prepared according to the methods of the invention, i.e., reductive amination in an aprotic solvent, include, but are not limited to, serotypes: 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38. The polysaccharides may be used in the form of oligosaccharides. These are conveniently formed by fragmentation of purified polysaccharide (e.g. by hydrolysis), which will usually be followed by purification of the fragments of the desired size.

In certain embodiments, one or more of serotypes 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, and 38 are prepared using reductive amination in an aprotic solvent. In certain aspects, pneumococcal polysaccharides from one or more of serotypes 1, 3, 4, 5, 9V, 11A, 12F, and 14 are prepared using reductive amination in an aprotic solvent. In certain aspects, pneumococcal polysaccharides from one or more of serotypes 2, 6C, 6D, 7B, 7C, 8, 9N, 15A, 15C, 16F, 17F, 19F, 20, 21, 22A, 23A, 23B, 24F, 27, 28A, 31, 34, 35A, 35B, 35F, and 38 are prepared using reductive amination in an aprotic solvent. In certain aspects, pneumococcal polysaccharides from one or both of serotypes 3 or 18C are conjugated to a carrier protein using reductive amination in an aprotic solvent. Polysaccharides from the other serotypes in a multivalent composition may be conjugated using reductive amination in an aprotic solvent or in an aqueous solvent. Polysaccharides from the other serotypes in a multivalent composition may also be conjugated using other chemistries which may be in an aprotic solvent or in an aqueous solvent.

Capsular polysaccharides from *Streptococcus pneumoniae* can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, each pneumococcal polysaccharide serotype is grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity in polysaccharide samples and/or to improve filterability for conjugated products using techniques such as mechanical or chemical sizing. Chemical hydrolysis maybe conducted using acetic acid. Mechanical sizing maybe conducted using High Pressure Homogenization Shearing.

In some embodiments, the purified polysaccharides before conjugation have a molecular weight of between 5 kDa and 4,000 kDa. Molecular weight can be calculated by size exclusion chromatography (SEC) combined with multiangle light scattering detector (MALS) and refractive index detector (RI). In other such embodiments, the polysaccharide has a molecular weight of between 10 kDa and 4,000 kDa; between 50 kDa and 4,000 kDa; between 50 kDa and 3,000 kDa; between 50 kDa and 2,000 kDa; between 50 kDa and 1,500 kDa; between 50 kDa and 1,000 kDa; between 50 kDa and 750 kDa; between 50 kDa and 500 kDa; between 100 kDa and 4,000 kDa; between 100 kDa and 3,000 kDa; 100 kDa and 2,000 kDa; between 100 kDa and 1,500 kDa; between 100 kDa and 1,000 kDa; between 100 kDa and 750 kDa; between 100 kDa and 500 kDa; between 100 and 400 kDa; between 200 kDa and 4,000 kDa; between 200 kDa and 3,000 kDa; between 200 kDa and 2,000 kDa; between 200 kDa and 1,500 kDa; between 200 kDa and 1,000 kDa; or between 200 kDa and 500 kDa.

The purified polysaccharides can be chemically activated to make the saccharides capable of reacting with the carrier protein. The purified polysaccharides can be connected to a linker. Once activated or connected to a linker, each capsular polysaccharide is separately conjugated to a carrier protein to form a glycoconjugate. The polysaccharide conjugates may be prepared by known coupling techniques.

The polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

The polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

The coupling can also take place indirectly, i.e. with an additional linker that is used to derivatise the polysaccharide prior to coupling to the linker.

The polysaccharide is coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker. The reaction results in a polysaccharide-additional linker intermediate in which the polysaccharide is coupled to the additional linker via a C—N linkage.

The polysaccharide can be coupled to the additional linker using a different group in the polysaccharide, particularly a carboxyl group. This coupling comprises two steps: (a1)

reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

In one embodiment, the chemical activation of the polysaccharides and subsequent conjugation to the carrier protein by reductive amination can be achieved by means described in U.S. Pat. Nos. 4,365,170, 4,673,574 and 4,902,506, U.S. Patent Application Publication Nos. 2006/0228380, 2007/184072, 2007/0231340 and 2007/0184071, and International Patent Application Publication Nos. WO2006/110381, WO2008/079653, and WO2008/143709). The chemistry may entail the activation of pneumococcal polysaccharide by reaction with any oxidizing agent which oxidizes a terminal hydroxyl group to an aldehyde, such as periodate (including sodium periodate, potassium periodate, or periodic acid). The reaction leads to a random oxidative cleavage of vicinal hydroxyl groups of the carbohydrates with the formation of reactive aldehyde groups.

In one embodiment, the polysaccharide is reacted with 0.01 to 10.0, 0.05 to 5.0, 0.1 to 1.0, 0.5 to 1.0, 0.7 to 0.8, 0.05 to 0.5, 0.1 to 0.3 molar equivalents of oxidizing agent. In a embodiment, the polysaccharide is reacted with about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 molar equivalents of oxidizing agent. It is generally preferable to use lower amounts of periodate for activation, for example, 0.1 to 0.3 Meq, in order to achieve limited polysaccharide activation (e.g., 0.05 to 0.22 or 0.09 to 0.22 moles of aldehyde/mole of polysaccharide repeat unit). As used herein, "activation level" refers to moles of aldehyde/mole of polysaccharide repeat unit. Less polysaccharide activation results in a more native like polysaccharide, i.e., fewer hydroxyl groups are converted to aldehydes.

In another embodiment, the duration of the oxidation reaction is between 1 hour and 50 hours, between 10 hours and 30 hours, between 15 hours and 20 hours, between 15 hours and 17 hours or about 16 hours.

In another embodiment, the temperature of the oxidation reaction is maintained between 15° C. and 45° C., between 15° C. and 30° C., between 20° C. and 25° C. In another embodiment, the temperature of the reaction is maintained at about 23° C.

Coupling to the carrier protein is by reductive amination via direct amination to the lysyl groups of the protein. For example, conjugation is carried out by reacting a mixture of the activated polysaccharide and carrier protein with a reducing agent such as sodium cyanoborohydride in the presence of nickel. The conjugation reaction may take place under aqueous solution or in the presence of dimethylsulfoxide (DMSO). See, e.g., U.S. Patent Application Publication Nos. US2015/0231270 and US2011/0195086 and European Patent No. EP 0471 177 B1. Unreacted aldehydes are then capped with the addition of a strong reducing agent, such as sodium borohydride.

Reductive amination involves two steps, (1) oxidation of the polysaccharide to form reactive aldehydes, and (2) reduction of the imine (Schiff base) formed between activated polysaccharide and a carrier protein to form a stable amine conjugate bond. Before oxidation, the polysaccharide is optionally size reduced. Mechanical methods (e.g. homogenization) or chemical hydrolysis may be employed. Chemical hydrolysis maybe conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^-$) and includes the various salts of periodate (e.g., sodium periodate and potassium periodate). In an embodiment, the capsular polysaccharide is oxidized in the presence of metaperiodate, preferably in the presence of sodium periodate ($NaIO_4$). In another embodiment the capsular polysaccharide is oxidized in the presence of orthoperiodate, preferably in the presence of periodic acid.

In an embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof In an aspect, said oxidant is a molecule bearing a N-halo moiety. In an aspect, said oxidant is selected from the group consisting of N-Chloro-Succinimide, N-Bromosuccinimide, N-lodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione.

In certain aspects, the oxidizing agent is 2,2,6,6-Tetramethyl-1-piperidinyloxy (TEMPO) free radical and N-Chlorosuccinimide (NCS) as the cooxidant (as described in International Patent Application Publication No. WO2014/097099). Therefore in one aspect, the glycoconjugates from *S. pneumoniae* are obtained by a method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent maybe selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

The second step of the conjugation process is the reduction of the imine (Schiff base) bond between activated polysaccharide and a carrier protein to form a stable conjugate bond (so-called reductive amination), using a reducing agent. Reducing agents which are suitable include the cyanoborohydrides (such as sodium cyanoborohydride or sodium borohydride). In one embodiment the reducing agent is sodium cyanoborohydride.

In certain embodiments of the methods of the invention, the reductive amination reaction is carried out in aprotic solvent (or a mixture of aprotic solvents). In an embodiment, the reduction reaction is carried out in DMSO or in DMF (dimethylformamide) solvent. The DMSO or DMF solvent may be used to reconstitute the activated polysaccharide and carrier protein, if lyophilized. In one embodiment, the aprotic solvent is DMSO.

At the end of the reduction reaction, there may be unreacted aldehyde groups remaining in the conjugates, which may be capped using a suitable capping agent. In one embodiment this capping agent is sodium borohydride ($NaBH_4$). Suitable alternatives include sodium triacetoxyborohydride or sodium or zinc borohydride in the presence of Bronsted or Lewis acids, amine boranes such as pyridine borane, 2-Picoline Borane, 2,6-diborane-methanol, dimethylamine-borane, t-BuMe'PrN—BH3, benzylamine-BH3 or 5-ethyl-2-methylpyridine borane (PEMB) or borohydride exchange resin. Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration, precipitation/elution, column chromatography (ion exchange chromatography, multimodal ion exchange chromatography, DEAE, or hydrophobic interaction chromatography), and depth filtration. In an embodiment, the glycoconjugates are purified by diafiltration or ion exchange chromatography or size exclusion chromatography.

Glycoconjugates prepared using reductive amination in an aprotic solvent are generally used in multivalent pneumococcal conjugate vaccines. Thus, in certain embodiments for multivalent compositions where not all the serotypes are prepared in an aprotic solvent, the reduction reaction for the remaining seroytpes is carried out in aqueous solvent (e.g., selected from PBS (phosphate buffered saline), MES (2-(N-morpholino)ethanesulfonic acid), HEPES, (4-(2-hydroxyethyl)-1-piperazineethanesulfonic acid), Bis-tris, ADA (N-(2-Acetamido)iminodiacetic acid), PIPES (piperazine-N,N'-bis(2-ethanesulfonic acid)), MOPSO (3-Morpholino-2-hydroxypropanesulfonic acid), BES (N,N-bis(2-hydroxyethyl)-2-aminoethanesulfonic acid), MOPS (3-(N-morpholino)propanesulfonic acid), DIPSO (3-Bis(2-hydroxyethyl) amino-2-hydroxypropane-1-sulfonic acid), MOBS (4-(N-morpholino)butanesulfonic acid), HEPPSO (N-(2-Hydroxyethyl)piperazine-N-(2-hydroxypropane-sulfonic acid)), POPSO (Piperazine-1,4-bis(2-hydroxy-3-propanesulfonic acid)), TEA (triethanolamine), EPPS (4-(2-Hydroxyethyl)piperazine-1-propanesulfonic acid), Bicine or HEPB, at a pH between 6.0 and 8.5, 7.0 and 8.0, or 7.0 and 7.5).

In some embodiments, the glycoconjugates of the present invention comprise a polysaccharide having a molecular weight of between 10 kDa and 10,000 kDa. In other such embodiments, the polysaccharide has a molecular weight of between 25 kDa and 5,000 kDa. In other such embodiments, the polysaccharide has a molecular weight of between 50 kDa and 1,000 kDa. In other such embodiments, the polysaccharide has a molecular weight of between 70 kDa and 900 kDa. In other such embodiments, the polysaccharide has a molecular weight of between 100 kDa and 800 kDa. In other such embodiments, the polysaccharide has a molecular weight of between 200 kDa and 600 kDa. In further such embodiments, the polysaccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa.

In some embodiments, the glycoconjugates of the present invention have a molecular weight of between 1,000 kDa and 10,000 kDa. In other such embodiments, the polysaccharide has a molecular weight of between 1,000 kDa and 7,000 kDa. In other such embodiments, the polysaccharide has a molecular weight of between 1,000 kDa and 6,000 kDa.

In certain embodiments, the conjugation reaction is performed by reductive amination wherein nickel is used for greater conjugation reaction efficiency and to aid in free cyanide removal. Transition metals are known form stable complexes with cyanide and are known to improve reductive methylation of protein amino groups and formaldehyde with sodium cyanoborohydride (S Gidley et al., *Biochem J.* 1982, 203: 331-334; Jentoft et al. Anal Biochem. 1980, 106: 186-190). By complexing residual, inhibitory cyanide, the addition of nickel increases the consumption of protein during the conjugation of and leads to formation of larger, potentially more immungenic conjugates.

Differences in starting cyanide levels in sodium cyanoborohydride reagent lots also lead to inconsistent conjugation performance, resulting in variable product attributes, such as conjugate size and conjugate Ps-to-$CRM_{197}$ ratio. The addition of nickel reduced conjugation inconsistency by complexing cyanide, eliminating differences in sodium cyanoborohydride lots.

Suitable alternative chemistries include the activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). For example, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18)

followed by reaction of with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

After conjugation of the capsular polysaccharide to the carrier protein, the polysaccharide-protein conjugates are purified (enriched with respect to the amount of polysaccharide-protein conjugate) by one or more of a variety of techniques. Examples of these techniques are well known to the skilled artisan and include concentration/diafiltration operations, ultrafiltration, precipitation/elution, column chromatography, and depth filtration. See, e.g., U.S. Pat. No. 6,146,902.

Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In an embodiment, the degree of conjugation of the glycoconjugate of the invention is between 2 and 18, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 18, between 5 and 13, between 7 and 18, between 7, and 13, between 8 and 18, between 8 and 13, between 10 and 18 or between 10 and 13. In an embodiment, the degree of conjugation of the glycoconjugate of the invention is about 2, about 3, about 4, about 5, about 6, about 7, about 8, about 9, about 10, about 11, about 12, about 13, about 14 or about 15. In an embodiment, the degree of conjugation of the glycoconjugate of the invention is between 7 and 18. In some such embodiments, the carrier protein is $CRM_{197}$.

The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In an embodiment, the ratio of capsular polysaccharide to carrier protein in the conjugate is between 0.9 and 1.1. In some such embodiments, the carrier protein is $CRM_{197}$. The glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In an embodiment, the glycoconjugate comprises less than about 50%, 45%, 40%, 35%, 30%, 25%, 20% or 15% of free polysaccharide compared to the total amount of polysaccharide. In an embodiment the glycoconjugate comprises less than about 25% of free polysaccharide compared to the total amount of polysaccharide. In an embodiment the glycoconjugate comprises less than about 20% of free polysaccharide compared to the total amount of polysaccharide. In an embodiment the glycoconjugate comprises less than about 15% of free polysaccharide compared to the total amount of polysaccharide.

Multivalent Polysaccharide-protein Conjugate Vaccines

Multivalent pneumococcal immunogenic compositions can comprise capsular polysaccharides from *S. pneumoniae* serotype selected from at least one of 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 conjugated to one or more carrier proteins, wherein a polysaccharide from at least one serotype is prepared using reductive amination in an aprotic solvent such as DMSO. The present invention contemplates multivalent pneumococcal immunogenic compositions having polysaccharides from at least 5, 6, 7, 8, 9, 10, 11, 12, 13, 14, 15, 16, 17, 18, 19, 20, 21, 22, 23, 24, or 25 serotypes. Preferably, saccharides from a particular serotype are not conjugated to more than one carrier protein.

In certain embodiments, polysaccharides from at least 5, 6, 7, 8, 9, 10, 11, 12, 13, 14, 15, 16, 17, 18, 19, 20, 21, 22, 23, 24, or 25 serotypes are prepared using reductive amination in an aprotic solvent such as DMSO.

In certain embodiments, one or more of serotypes 3, 6A, 6B, 7F, 18C, 19A, 19F, or 23F are prepared using reductive amination in an aprotic solvent. In certain aspects of this embodiment, one or both of serotypes 3 or 18C are prepared using reductive amination in an aprotic solvent.

In certain embodiments, at least 30, 35, 40, 45, 50, 55, 60, 65, 70, 75, 80, 85, 90, 95, or 100% of the serotypes in a multivalent composition are prepared in an aprotic solvent. The remainder of the serotypes are prepared using an alternative chemistry and/or in an aqueous solvent.

In certain embodiments, one or more of serotypes 1, 2, 3, 4, 5, 6C, 6D, 7B, 7C, 8, 9N, 9V, 11A, 12F, 14, 15A, 15C, 16F, 17F, 18C, 20, 21, 22A, 23A, 23B, 24F, 27, 28A, 31, 34, 35A, 35B, 35F, and 38 are prepared using reductive amination in an aprotic solvent. In certain aspects, one or more of serotypes 1, 3, 4, 5, 9V, 11A, 12F, and 14 are prepared using reductive amination in an aprotic solvent. In certain aspects, one or more of serotypes 2, 6C, 6D, 7B, 7C, 8, 9N, 15A, 15C, 16F, 17F, 19F, 20, 21, 22A, 23A, 23B, 24F, 27, 28A, 31, 34, 35B, 35F, and 38 are prepared using reductive amination in an aprotic solvent.

In one embodiment, a multivalent composition consists of polysaccharides from serotypes 6A, 6B, 7F, 18C, 19A, 19F, and 23F prepared using reductive amination in an aprotic solvent such as DMSO and polysaccharides from serotypes 1, 3, 4, 5, 9V, 14, 22F and 33F prepared using reductive amination in an aqueous solvent.

After the individual glycoconjugates are purified, they are compounded to formulate the immunogenic composition of the present invention. These pneumococcal conjugates are prepared by separate processes and bulk formulated into a single dosage formulation.

Carrier Protein

In a particular embodiment of the present invention, $CRM_{197}$ is used as the carrier protein. $CRM_{197}$ is a non-toxic variant (i.e., toxoid) of diphtheria toxin. In one embodiment, it is isolated from cultures of *Corynebacterium diphtheria* strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in *Pseudomonas fluorescens* using Pfenex Expression Technology™ (Pfenex Inc., San Diego, Calif.).

Other suitable carrier proteins include additional inactivated bacterial toxins such as DT (Diphtheria toxoid) or fragment B of DT (DTFB), TT (tetanus toxid) or fragment C of TT, pertussis toxoid, cholera toxoid (e.g., as described in International Patent Application Publication No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can be used as the second carrier protein, such as $CRM_{176}$, $CRM_{228}$, $CRM_{45}$ (Uchida et al., 1973, J Biol Chem 218:3838-3844); $CRM_9$, $CRM_{45}$, $CRM_{102}$, $CRM_{103}$ and $CRM_{107}$ and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711. Such DT mutants can also be used to make DTFB variants where the variants comprise the B fragment contain the epitope regions.

Where multivalent vaccines are used, a second carrier can be used for one or more of the antigens in a multivalent vaccine. The second carrier protein is preferably a protein that is non-toxic and non-reactogenic and obtainable in sufficient amount and purity. The second carrier protein is also conjugated or joined with an antigen, e.g., a *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

Pharmaceutical/Vaccine Compositions

The present invention further provides compositions, including pharmaceutical, immunogenic and vaccine compositions, comprising, consisting essentially of, or alternatively, consisting of any of the polysaccharide serotype combinations described above together with a pharmaceutically acceptable carrier and an adjuvant.

Formulation of the polysaccharide-protein conjugates of the present invention can be accomplished using art-recognized methods. For instance, individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In an embodiment, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% TWEEN® 80, and 0.5% Span 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% TWEEN® 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% TWEEN® 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, Mass.) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion;

(5) synthetic polynucleotides such as oligonucleotides containing CpG motif(s) (U.S. Pat. No. 6,207,646);

(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, SUPERFOS®, Amphogel, aluminum (III) hydroxide, aluminum hydroxyphosphate sulfate, Aluminum Phosphate Adjuvant (APA), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available Al(OH)₃ (e.g. Alhydrogel or SUPERFOS® of Denmark/Accurate Chemical and Scientific Co., Westbury, N.Y.) is used to adsorb proteins in a ratio of 50-200 g protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of antigen that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted to target 8 μg/mL for all serotypes except 6B, which will be diluted to target 16 μg/mL. Once diluted, the batch will be filter sterilized, and an equal volume of aluminum phosphate adjuvant added aseptically to target a final aluminum concentration of 250 μg/mL. The adjuvanted, formulated batch will be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to infection, e.g., a pneumococcal infection, by means of administering the vaccine via a systemic or mucosal route. In one embodiment, the present invention provides a method of inducing an immune response to a S. pneumoniae capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunogically effective amount of a immunogenic composition of the present invention.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically. We have demonstrated that the vaccine is immunogenic in Infant Rhesus Monkey animal data.

"Effective amount" of a composition of the invention refers to a dose required to elicit antibodies that significantly reduce the likelihood or severity of infectivitiy of a microbe, e.g., *S. pneumonia*, during a subsequent challenge.

The methods of the invention can be used for the prevention and/or reduction of primary clinical syndromes caused by microbes, e.g., *S. pneumonia*, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 μg of each polysaccharide, particularly 0.1 to 10 μg, and more particularly 1 to 5 μg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 μg.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 μg, or 1, 1.2, 1.5, 2, 3, 5 mg or more. In yet another embodiment, the dose of alum salt described above is per μg of recombinant protein.

According to any of the methods of the present invention and in one embodiment, the subject is human. In certain embodiments, the human subject is an infant (less than 1 year of age), toddler (approximately 12 to 24 months), or young child (approximately 2 to 5 years). In other embodiments, the human subject is an elderly subject (e.g., >50 years old or >65 years old). The compositions of this invention are also suitable for use with older children, adolescents and adults (e.g., aged 18 to 45 years or 18 to 65 years).

In one embodiment of the methods of the present invention, a composition of the present invention is administered as a single inoculation. In another embodiment, the vaccine is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by *S. pneumoniae* is 2, 4, 6 and 12-15 months of age. Thus, in an embodiment, the composition is administered as a 4-dose series at 2, 4, 6, and 12-15 months of age.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761.

Formulations

The compositions of the invention can be administered to a subject by one or more methods known to a person skilled in the art, such as parenterally, transmucosally, transdermally, intramuscularly, intravenously, intra-dermally, intranasally, subcutaneously, intra-peritonealy, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of TRIS, acetate, glutamate, lactate, maleate, tartrate, phosphate, citrate, carbonate, glycinate, histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the invention may also contain a surfactant. Surfactants include, but are not limited to: the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON™ X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as BRIJ™ surfactants), such as triethyleneglycol monolauryl ether (BRIJ™ 30); and sorbitan esters (commonly known as the SPANs), such as sorbitan trioleate (Span 85) and sorbitan monolaurate. A preferred surfactant for including in the emulsion is PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (TRITON™ X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as PS-80) 0.01 to 1%, in particular about 0.1%; octyl- or nonylphenoxy polyoxyethanols (such as TRITON™ X-100, or other detergents in the TRITON™ series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

In certain embodiments, the composition consists essentially of histidine (20 mM), saline (150 mM) and 0.02% PS-20 or 0.04% PS-80 at a pH of 5.8 with 250 ug/mL of APA (Aluminum Phosphate Adjuvant). PS-20 can range from 0.005% to 0.1% (w/v) with the presence of PS-20 or PS-80 in formulation controlling aggregation during simulated manufacture and in shipping using primary packaging. Process consists of combining blend of up to 24 serotypes in histidine, saline, and PS-20 or PS-80 then combining this blended material with APA and saline with or without antimicrobial preservatives.

The choice of surfactant may need to be optimized for different drug products and drug substances. For multivalent vaccines having 15 or more serotypes, PS-20 and P188 are preferred. The choice of chemistry used to make conjugate can also play an important role in the stabilization of the formulation. In particular, when the conjugation reactions used to prepare different polysaccharide protein conjugates in a multivalent composition include both aqueous solvent and DMSO solvent, has found that particular surfactant systems provide significant differences in stability. Improved stability of polysachharide protein conjugates was seen with polysorbate 20 alone or with poloxamer 188 in combination with a polyol.

The exact mechanism of how a specifc detergent protects a biotherapeutic is poorly understood and cannot be predicted a priori. Possible stabilization mechanisms include preferential hydration, preferential exclusion, air/liquid interface competition between biotherapeutic and surface, surface tension, and/or direct association of the detergent with the biotherpeutic to mask hydrophobic patches which serve as seeds for aggregation.

Poloxamer may also be used in the compositions of the invention. A poloxamer is a nonionic triblock copolymer composed of a central hydrophobic chain of polyoxypropylene (poly(propylene oxide)) flanked by two hydrophilic chains of polyoxyethylene (poly(ethylene oxide)). Poloxamers are also known by the tradename Pluronic®. Because the lengths of the polymer blocks can be customized, many different poloxamers exist that have slightly different properties. For the generic term "poloxamer", these copolymers are commonly named with the letter "P" (for poloxamer) followed by three digits, the first two digits x 100 give the approximate molecular mass of the polyoxypropylene core, and the last digit x 10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit x 10 gives the percentage polyoxyethylene content (e.g., L61=Pluronic® with a polyoxypropylene molecular mass of 1,800 g/mol and a 10% polyoxyethylene content). See U.S. Pat. No. 3,740,421.

Examples of poloxamers have the general formula:

$$HO(C_2H_4O)_a(C_3H_6O)_b(C_2H_4O)_aH,$$

wherein a and b blocks have the following values:

| Pluronic ® | Poloxamer | a | b | Molecular Weight |
|---|---|---|---|---|
| L31 | | 2 | 16 | 1100 (average) |
| L35 | | | | 1900 (average) |
| L44NF | 124 | 12 | 20 | 2090 to 2360 |
| L64 | | | | 2900 (average) |
| L81 | | | | 2800 (average) |
| L121 | | | | 4400 (average) |
| P123 | | 20 | 70 | 5750 (average) |
| F68NF | 188 | 80 | 27 | 7680 to 9510 |
| F87NF | 237 | 64 | 37 | 6840 to 8830 |
| F108NF | 338 | 141 | 44 | 12700 to 17400 |
| F127NF | 407 | 101 | 56 | 9840 to 14600 |

Molecular weight units, as used herein, are in Dalton (Da) or g/mol.

Preferably, the poloxamer generally has a molecular weight in the range from 1100 to 17,400 Da, from 7,500 to 15,000 Da, or from 7,500 to 10,000 Da. The poloxamer can be selected from poloxamer 188 or poloxamer 407. The final concentration of the poloxamer in the formulations is from 0.001% to 5% weight/volume, or 0.025% to 1% weight/volume. In certain aspects, the polyol is propylene glycol and is at final concentration from 1% to 20% weight/volume. In certain aspects, the polyol is polyethylene glycol 400 and is at final concentration from 1% to 20% weight/volume.

Suitable polyols for the formulations of the invention are polymeric polyols, particularly polyether diols including, but are not limited to, propylene glycol and polyethylene glycol, Polyethylene glycol monomethyl ethers. Propylene glycol is available in a range of molecular weights of the monomer from ~425 to ~2700. Polyethylene glycol and Polyethylene glycol monomethyl ether is also available in a range of molecular weights ranging from ~200 to 35000 including but not limited to PEG200, PEG300, PEG400, PEG1000, PEG MME 550, PEG MME 600, PEG MME 2000, PEG MME 3350 and PEG MME 4000. A preferred polyethylene glycol is polyethylene glycol 400. The final concentration of the polyol in the formulations of the invention may be 1% to 20% weight/volume or 6% to 20% weight/volume.

The formulation also contains a pH-buffered saline solution. The buffer may, for example, be selected from the group consisting of TRIS, acetate, glutamate, lactate, maleate, tartrate, phosphate, citrate, carbonate, glycinate, histidine, glycine, succinate, HEPES (4-(2-hydroxyethyl)-1-piperazineethanesulfonic acid), MOPS (3-(N-morpholino)propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspect of the invention, the buffer selected from the group consisting of phosphate, succinate, histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is histidine at a final concentration of 5 mM to 50 mM, or succinate at a final concentration of 1 mM to 10 mM. In certain aspects, the histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but are not limited to 25 mM to 500 mM or 40 mM to 170 mM. In one aspect, the saline is NaCl, optionally present at a concentration from 20 mM to 170 mM.

In an embodiment, the formulatons comprise a L-histidine buffer with sodium chloride.

In certain embodiments of the formulations described herein, the polysaccharide-protein conjugates comprise one or more pneumococcal polysaccharides conjugated to a carrier protein. The carrier protein can be selected from $CRM_{197}$, diphtheria toxin fragment B (DTFB), DTFBC8, Diphtheria toxoid (DT), tetanus toxoid (TT), fragment C of TT, pertussis toxoid, cholera toxoid, *E. coli* LT, *E. coli* ST, exotoxin A from *Pseudomonas aeruginosa*, and combinations thereof. In one aspect, all of the polysaccharide-protein conjugates are prepared using aqueous chemisty. In another aspect, one or more of the polysaccharide protein conjugates are prepared using DMSO solvent. As an example, the polysaccharide-protein conjugate formulation can be a 15-valent pneumococcal conjugate (15 vPnC) formulation wherein polysaccharide protein conjugates from serotypes 6A, 6B, 7F, 18C, 19A, 19F, and 23F are prepared using DMSO solvent and polysaccharide protein conjugates from serotypes 1, 3, 4, 5, 9V, 14, 22F, and 33F are prepared using aqueous solvent.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761. Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Example 1: Preparation of S. *Pneumoniae* Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP0497524. Isolates of pneumococcal subtypes are available from the American Type Culture Collection (Manassas, Va.). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the *S. pneumococcus* serotypes present were obtained from the Merck Culture Collection (Rahway, N.J.) in a frozen vial. A thawed seed culture was transferred to the seed fermentor containing a pre-sterilized growth media appropriate for *S. pneumoniae*. The culture was grown in the seed fermentor with temperature and pH control. The entire volume of the seed fermentor was transferred to a production fermentor containing pre-sterilized growth media. The production fermentation was the final cell growth stage of the process. Temperature, pH, and the agitation rate were controlled.

The fermentation process was terminated via the addition of an inactivating agent. After inactivation, the batch was transferred to the inactivation tank where it was held at controlled temperature and agitation. Cell debris was removed using a combination of centrifugation and filtration. The batch was ultrafiltered and diafiltered. The batch was then subjected to solvent-based fractionations that remove impurities and recover polysaccharide.

Example 2: Conjugation of Serotypes 1, 3, 4, 5, 6A, 6B, 7F, 9V, 14, 18C, 19A, 19F, 22F, 23F, and 33F to $CRM_{197}$ Using Reductive Amination in Aqueous Solution The different polysaccharide serotypes were individually conjugated to purified $CRM_{197}$ carrier protein using a common process flow. Polysaccharide was dissolved, size reduced, chemically activated and buffer-exchanged by ultrafiltration. Purified $CRM_{197}$ was then conjugated to the activated polysaccharide utilizing $NiCl_2$ (2 mM) in the reaction mixture, and the resulting conjugate was purified by ultrafiltration prior to a final 0.2-micron filtration. Several process parameters within each step, such as pH, temperature, concentration, and time were controlled to serotype-specific values in section below.

Polysaccharide Size Reduction and Oxidation

Purified pneumococcal capsular polysaccharide powder was dissolved in water, and all serotypes, except serotype 19A, were 0.45-micron filtered. All serotypes, except serotype 19A, were homogenized to reduce the molecular mass of the polysaccharide. Serotype 19A was not size reduced due to its relatively low starting size. Homogenization pressure and number of passes through the homogenizer were controlled to serotype-specific targets (150-1000 bar; 4-7 passes) to achieve a serotype-specific molecular mass. Size-reduced polysaccharide was 0.2-micron filtered and then concentrated and diafiltered against water using a 10 kDa NMWCO tangential flow ultrafiltration membrane.

The polysaccharide solution was then adjusted to a serotype-specific temperature (4-22° C.) and pH (4-5) with a sodium acetate buffer to minimize polysaccharide size reduction due to activation. For all serotypes (except serotype 4), polysaccharide activation was initiated with the addition of a 100 mM sodium metaperiodate solution. The amount of sodium metaperiodate added was serotype-specific, ranging from approximately 0.1 to 0.5 moles of sodium metaperiodate per mole of polysaccharide repeating unit. The serotype-specific charge of sodium metaperiodate was to achieve a target level of polysaccharide activation (moles aldehyde per mole of polysaccharide repeating unit). For serotype 4, prior to the sodium metaperiodate addition, the batch was incubated at approximately 50° C. and pH 4.1 to partially deketalize the polysaccharide.

For all serotypes, with the exception of serotypes 5 and 7F, the activated product was diafiltered against 10 mM potassium phosphate, pH 6.4 using a 10 kDa NMWCO tangential flow ultrafiltration membrane. Serotypes 5 and 7F were diafiltered against 10 mM sodium acetate. Ultrafiltration for all serotypes was conducted at 2-8° C.

Polysaccharide conjugation to $CRM_{197}$

Oxidized polysaccharide solution was mixed with water and 1.5 M potassium phosphate, pH 6.0 or pH 7.0, depending on the serotype. The buffer pH selected was to improve the stability of activated polysaccharide during the conjugation reaction. Purified $CRM_{197}$, obtained through expression in *Pseudomonas fluorescens* as previously described (WO 2012/173876 A1), was 0.2-micron filtered and combined with the buffered polysaccharide solution at a polysaccharide to $CRM_{197}$ mass ratio ranging from 0.4 to 1.0 w/w depending on the serotype. The mass ratio was selected to control the polysaccharide to $CRM_{197}$ ratio in the resulting conjugate. The polysaccharide and phosphate concentrations were serotype-specific, ranging from 3.6 to 10.0 g/L and 100 to 150 mM, respectively, depending on the serotype. The serotype-specific polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for a serotype-specific duration (72 to 120 hours) to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. All serotypes (except serotype 5) were diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added. Serotype 5 was diafiltered against 300 mM potassium phosphate using a 100 kDa NMWCO tangential flow ultrafiltration membrane.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. The retentate batch was 0.2 micron filtered.

Serotype 19F conjugate was incubated for approximately 7 days at 22° C., diafiltered against 10 mM L-histidine in 150 mM sodium chloride, pH 7.0 at 4° C. using a 100 kDa NMWCO tangential flow ultrafiltration membrane, and 0.2-micron filtered.

The batch was adjusted to a polysaccharide concentration of 1.0 g/L with additional 10 mM L-histidine in 150 mM sodium chloride, pH 7.0. The batch was dispensed into aliquots and frozen at ≤−60° C.

Example 3: Methods for the Conjugation of Serotypes 3, 4, 6A, 6B, 7F, 9V, 14, 18C, 19A, 19F, 22F, 23F, and 33F to $CRM_{197}$ Using Reductive Amination in Dimethylsulfoxide The different polysaccharide serotypes 3, 4, 6A, 6B, 7F, 9V, 14, 18C, 19A, 19F, 22F, 23F, and 33F were individually conjugated to the purified $CRM_{197}$ carrier protein using a common process flow. Polysaccharide was dissolved, sized to a target molecular mass, chemically activated and buffer-exchanged by ultrafiltration. Activated polysaccharide and purified $CRM_{197}$ were individually lyophilized and redissolved in dimethylsuloxide (DMSO). Redissolved polysaccharide and $CRM_{197}$ solutions were then combined and conjugated as described below. The resulting conjugate was purified by ultrafiltration prior to a final 0.2-micron filtration. Several process parameters within each step, such as pH, temperature, concentration, and time were controlled to serotype-specific values in section below.

Polysaccharide Size Reduction and Oxidation

Purified pneumococcal capsular Ps powder was dissolved in water, and all serotypes, except serotype 19A, were 0.45-micron filtered. All serotypes, except serotypes 18C and 19A, were homogenized to reduce the molecular mass of the Ps. Homogenization pressure and number of passes through the homogenizer were controlled to serotype-specific targets (150-1000 bar; 4-7 passes). Serotype 18C was size-reduced by acid hydrolysis at ≥90° C.

Size-reduced polysaccharide was 0.2-micron filtered and then concentrated and diafiltered against water using a 10 kDa NMWCO tangential flow ultrafiltration membrane. A 5 kDa NMWCO membrane was used for serotype 18C.

The polysaccharide solution was then adjusted to a serotype-specific temperature (4-22° C.) and pH (4-5) with a sodium acetate buffer to minimize polysaccharide size reduction due to activation. For all serotypes (except serotype 4), polysaccharide activation was initiated with the addition of a 100 mM sodium metaperiodate solution. The amount of sodium metaperiodate added was serotype-specific, ranging from approximately 0.1 to 0.5 moles of sodium metaperiodate per mole of polysaccharide repeating unit. The serotype-specific charge of sodium metaperiodate was to achieve a target level of polysaccharide activation (moles aldehyde per mole of polysaccharide repeating unit). For serotype 4, prior to the sodium metaperiodate addition, the batch was incubated at approximately 50° C. and pH 4.1 to partially deketalize the polysaccharide.

The activated product was diafiltered against 10 mM potassium phosphate, pH 6.4 using a 10 kDa NMWCO tangential flow ultrafiltration membrane, then diafiltered or dialyzed against water using a 10 kDa NMWCO membrane. A 5 kDa NMWCO membrane was used for serotype 18C. Ultrafiltration or dialysis for all serotypes was conducted at 2-8° C.

Polysaccharide Conjugation to $CRM_{197}$

Purified $CRM_{197}$, obtained through expression in Pseudomonas fluorescens as previously described (WO 2012/173876 A1), was diafiltered against 2-5 mM phosphate, pH 7.0 buffer using a 5 kDa NMWCO tangential flow ultrafiltration membrane and 0.2-micron filtered.

For serotypes other than serotype 3, the oxidized polysaccharides were formulated at 6 mg Ps/mL and 5% w/v sucrose (50 mg sucrose/mL) in water. For serotype 3, the oxidized polysaccharide was formulated at 2 mg Ps/mL and 10% w/v sucrose (100 mg sucrose/mL) in water. The protein solution was formulated at 6 mg Pr/mL with 1% w/v sucrose (10 mg sucrose/mL) in phosphate buffer.

Formulated Ps and $CRM_{197}$ solutions were individually lyophilized. Lyophilized Ps and $CRM_{197}$ materials were redissolved in DMSO and combined using a mixing tee. Sodium cyanoborohydride (1 moles per mole of polysaccharide repeating unit) was added, and conjugation proceeded for a serotype-specific duration (1 to 48 hours) to achieve a targeted conjugate size.

Reduction with Sodium Borohydride

Sodium borohydride (2 moles per mole of polysaccharide repeating unit) was added following the conjugation reaction. The batch was diluted into 150 mM sodium chloride, with or without approximately 0.025% (w/v) polysorbate 20, at approximately 4° C. Potassium phosphate buffer was then added to neutralize the pH. For serotypes 3, 6A, 6B, 7F, 9V, 18C, 19A, 19F, 22F, 23F, and 33F, the batch was concentrated and diafiltered at approximately 4° C. against 150 mM sodium chloride, with or without 25 mM potassium phosphate pH 7, using a 30 kDa NMWCO tangential flow ultrafiltration membrane.

Final Filtration and Product Storage

Serotypes 3, 6A, 6B, 7F, 9V, 18C, 19A, 22F, 23F, and 33F were concentrated and diafiltered against 10 mM histidine in 150 mM sodium chloride, pH 7.0, with or without 0.015% (w/v) polysorbate 20, at 4° C. using a 300 kDa NMWCO tangential flow ultrafiltration membrane. The retentate batch was 0.2 micron filtered.

Serotype 19F was incubated for approximately 5 days, diafiltered against 10 mM histidine in 150 mM sodium chloride, pH 7.0 at approximately 4° C. using a 300 kDa NMWCO tangential flow ultrafiltration membrane, and 0.2-micron filtered.

Serotypes 3, 6A, 6B, 7F, 9V, 18C, 19A, 19F, 22F, 23F, and 33F were diluted with additional 10 mM histidine in 150 mM sodium chloride, pH 7.0, dispensed into aliquots and frozen at ≤−60° C.

Serotypes 4 and 14 were dialyzed against 150 mM sodium chloride at approximately 4° C. using a 300 kDa NMWCO membrane, 0.2-micron filtered, dispensed into aliquots and frozen at ≤−60° C.

Example 4: Analysis of Conjugates

Molecular Weight and Concentration Analysis of Conjugates Using HPSEC/UV/MALS/RI Assay Conjugate samples were injected and separated by high performance size-exclusion chromatography (HPSEC). Detection was accomplished with ultraviolet (UV), multi-angle light scattering (MALS) and refractive index (RI) detectors in series. Protein concentration was calculated from UV280 using an extinction coefficient. Polysaccharide concentration was deconvoluted from the RI signal (contributed by both protein and polysaccharide) using the do/dc factors which are the change in a solution's refractive index with a change in the solute concentration reported in mL/g. Average molecular weight of the samples were calculated by Astra software (Wyatt Technology Corporation, Santa Barbara, Calif.) using the measured concentration and light scattering information across the entire sample peak.

Polysaccharide Degree of Activation Assay

Conjugation occurs through reductive amination between the activated aldehydes and mainly lysine residues on the carrier protein. The level of activation, as represented by moles of aldehyde per moles of polysaccharide repeat unit, is important to control the conjugation reactions. An assay for measure the degree of activation is described in U.S. Patent Application Publication No. 2017/0021006.

An internal assay was developed to measure the degree of activation based on reaction of aldehyde groups (created during periodate oxidation of the polysaccharide) with thiosemicarbazide (available from commercial sources).

Quantification can be achieved by NMR (nuclear magnetic resonance) or by comparing the derivatized polysaccharide to appropriate reference standards and/or through the use of extinction coefficients of the derivative. The use of extinction coefficients for this assay is similar to its use in HPSEC/UV/MALS/RI method.

Generally, the assay can be run under the following for reaction conditions:

Time: 0.5 h-35 hr (this is serotype specific, but the reaction is followed until completion, i.e., plateaus in a time course)

Temperature: 15° C.-37° C., preferably around 21-27° C.

TSC concentration: 1-5 mg/mL pH of reaction: pH 3-5.5, preferably 4.0

For Example 4, polysaccharide was derivatized with 1.25 to 2.5 mg/mL thiosemicarbazide (TSC) at pH 4.0 to introduce a chromophore (derivatization of activated polysaccharide for serotypes 1, 5, and 9V uses 1.25 mg/mL TSC). The derivatization reaction was allowed to proceed to reach a plateau. The actual time varied depending on reaction speed for each serotype. TSC-Ps was then separated from TSC and other low molecular weight components by high performance size exclusion chromatography. The signal was detected by UV absorbance at 266 nm. The level of activated aldehyde is calculated against either standard curve injections of Mono-TSC or directly using predetermined extinction coefficients. Mono-TSC is a synthesized thiosemicarbazone derivative of monosaccharide. The aldehyde level is then converted to moles of aldehyde per mole of repeat unit (Ald/RU) using the Ps concentration measured by HPSEC/UV/MALS/RI assay.

Similar derivatization can be conducted with thiosemicarbazide structural analogs, hydrazides, hydrazine, semicarbazide, semicarbazide structural analogs, aminooxy compounds or aromatic amines as long as the derivatives have significant UV absorbance. The UV absorbance could be from the chromophore attached to the derivatization agents, or a chromophore generated as a result of the aldehyde derivatization, as the case of thiosemicarbazide.

Determination of Lysine Consumption in Conjugated Protein as a Measure of the Number of Covalent Attachments Between Polysaccharide and Carrier Protein The Waters AccQ-Tag amino acid analysis (AAA) was used to measure the extent of conjugation in conjugate samples. Samples were hydrolyzed using vapor phase acid hydrolysis in the Eldex workstation, to break the carrier proteins down into their component amino acids. The free amino acids were derivatized using 6-aminoquinolyl-N-hydroxysuccinimidyl carbamate (AQC). The derivatized samples were then analyzed using UPLC with UV detection on a C18 column. The average protein concentration was obtained using representative amino acids other than lysine. Lysine consumption during conjugation (i.e., lysine loss) was determined by the difference between the average measured amount of lysine in the conjugate and the expected amount of lysine in the starting protein.

Attributes of Conjugates Made Using Reductive Amination in Aqueous and DMSO Solutionss Polysaccharide activation and lysine consumption (i.e., lysine loss) results for conjugates generated using the processes described in Examples 2 and 3 are listed in Table 1. There is a clear distinction that conjugates made in DMSO (Example 3) had higher lysine consumption with lower polysaccharide activation than conjugates made in aqueous solution (Example 2). This suggests that preparing the conjugates in DMSO solution allows the polysaccharide to attach to more conjugation sites on the carrier protein with less activation or destruction to native polysaccharide structures. As a result, the conjugates on average contain more glycopeptide per polysaccharide repeating unit due to higher cross-linking in conjugates prepared in DMSO solution than in aqueous solution. It is believed that the glycopeptide is the antigenic domain to which an immune response is generated. Consequently, conjugates generated in DMSO are expected to be more immunogenic that conjugates generate in aqueous solution.

The average molecular weight (Mw) of the conjugates in Table 1 were measured by the HPSEC UV-MALS-RI assay. Conjugates generated by reductive amination in aqueous solution ranged from 990 to 3410 kDa. Conjugates generated in DMSO were generally larger with sizes ranging from 1300 to 5822 kDa.

TABLE 1

Lysine loss for pneumococcal serotype 3, 4, 6A, 6B, 7F, 9V, 14, 18C, 19A, 19F, and 23F $CRM_{197}$ conjugates made using reductive amination in aqueous solution or in DMSO.

| Conjugate | Conjugate Lot # | Conjugation reaction in aqueous or DMSO solution | Polysaccharide activation (mole aldehyde/mole repeat unit) | Lysine loss (mol/mol protein) |
|---|---|---|---|---|
| Serotype 3-$CRM_{197}$ | 1 | Aqueous | 0.10 | 3.1 |
| | 2 | | 0.10 | 2.5 |
| | 3 | | 0.10 | 3.1 |
| | 4 | DMSO | 0.092 | 16.3 |
| | 5 | | 0.053 | 9.6 |
| Serotype 4-$CRM_{197}$ | 1 | Aqueous | 0.43 | 2.7 |
| | 2 | DMSO | 0.25 | 3.0 |
| Serotype 6A-$CRM_{197}$ | 1 | Aqueous | 0.19 | 4.5 |
| | 2 | DMSO | 0.11 | 9.1 |
| Serotype 6B-$CRM_{197}$ | 1 | Aqueous | 0.18 | 4.6 |
| | 2 | DMSO | 0.11 | 9.6 |
| Serotype 7F-$CRM_{197}$ | 1 | Aqueous | 0.26 | 2.0 |
| | 2 | DMSO | 0.22 | 10.6 |
| Serotype 9V-$CRM_{197}$ | 1 | Aqueous | 0.30 | 4.7 |
| | 2 | DMSO | 0.15 | 7.9 |
| Serotype 14-$CRM_{197}$ | 1 | Aqueous | 0.22 | 6.4 |
| | 2 | DMSO | 0.22 | 12.7 |
| Serotype 18C-$CRM_{197}$ | 1 | Aqueous | 0.12 | 3.5 |
| | 2 | DMSO | 0.11 | 9.2 |
| Serotype 19A-$CRM_{197}$ | 1 | Aqueous | 0.38 | 4.9 |
| | 2 | DMSO | 0.14 | 9.5 |
| Serotype 19F-$CRM_{197}$ | 1 | Aqueous | 0.13 | 2.7 |
| | 2 | DMSO | 0.15 | 9.6 |
| Serotype 22F-$CRM_{197}$ | 1 | Aqueous | 0.12 | 1.7 |
| | 2 | DMSO | 0.15 | 7.2 |
| | 3 | | 0.15 | 7.0 |
| Serotype 23F-$CRM_{197}$ | 1 | Aqueous | 0.39 | 3.2 |
| | 2 | DMSO | 0.19 | 10.8 |
| Serotype 33F-$CRM_{197}$ | 1 | Aqueous | 0.23 | 4.5 |
| | 2 | DMSO | 0.14 | 7.0 |

Quantification of the Extent of Conjugation at Different Sites on $CRM_{197}$

Polysaccharide can be conjugated either to the amine group at the N-terminus of the carrier protein or to any of the side chains of the 39 lysine residues in $CRM_{197}$. The amino acid sequence of $CRM_{197}$ is provided in Table 2, where the lysines (abbreviated as K) are underlined and in bold. To locate and quantify the extent of polysaccharide conjugation at the different sites on $CRM_{197}$ protein, an LC/UV/MS peptide mapping method was used. Representative conjugate samples (prepared with DMSO or aqueous solution)

were digested in duplicate with trypsin, producing tryptic peptides. The mixtures were then separated on a reversed phase $C_{18}$ column and analyzed by UV and mass spectrometer. A $CRM_{197}$ protein sample (not conjugated with a polysaccharide) was also processed in triplicate at the same time as a control. Since trypsin cleaves a protein on the C-terminal side of lysine and arginine residues, conjugation at a lysine residue makes that site protease resistant. The extent of conjugation at a particular site was determined by calculating a decrease of peak intensity of a tryptic peptide as compared to a $CRM_{197}$ control. Depending on the cleavage sites and sequences, the signal decrease of a particular peptide could be due to mis-cleavage of the lysines at the preceeding peptide, or mis-cleavage of the lysine at the end of the peptide, or conjugation in the middle of the peptide sequence.

The relative percentages of peptide signal decrease for serotype 19A conjugates compared to $CRM_{197}$ control were plotted against possible sites of conjugation in FIG. 1. The lysine locations listed in the x-axis were numbered based on their order on the $CRM_{197}$ protein sequence, and represent possible conjugation sites of the analyzed peptides. For example, "33" means the peptide signal decrease was due to conjugation at the 33rd lysine; and "6, 7" means the peptide signal descrease was due to conjugation at the 6th, or the 7th, or both lyines. The data in FIG. 1 suggested that not only the extent of conjugation at each site was generally higher for conjugates prepared in DMSO compared to aqueous solution, there were also more sites of conjugation in DMSO. Those additional conjugation sites include the 29th, 30th, 31st, and 32nd lysines, which were only lysines located in previously identified common human T-cell peptide epitopes (See Raju et al., 1995, Eur. J. Immunol. 25:3207-3214, located in peptide 411-430 and peptide 431-450 of $CRM_{197}$ sequence). Similar results were observed with other serotypes tested.

TABLE 2

$CRM_{197}$ amino acid sequence

| Amino Acid | Amino Acid Sequence |
|---|---|
| 1-535 | JDGGYYGVVN#VIYPHQIVV\#KJWNSJ\YGV#LTNJLTNSNV#JWTJQ\GGGZNHI\VWGQN\#GDDJ\VYGQH#QSOVJNDJJY#YNYW\SJOWN#YODONYGQDHWLNNHOJOVO#WHSOPHTYJW#HHILNUIJGJ#DVUYYOVOSI#DHJVVVYH\LQQZHTDNDOV#YHOHLQIHWU#JNUJTGDP\H#\PDTDFDJQU#YUUVYJVVOVFLQOGZGYLU#GNWNWNLHVO#NHKJSLNQNP#VHVSQNWYVH#HNDNT\OHHIKTWDOHKSHO#VHONWYWJWQ#SYIDJDQ\DD#ZDYQYDTYLG#VHWDGQOHNWWDDOVLOSJL#JVYPJLDGJD#YKKQWHHLYD#TVLDOVVOPY#DTDLSOYJHOYGLJIDD\QI#YHVLLQOITY#YKQV\QUSD\#VSJKNWTSIO#KGJ\DYVZQWYHGVLLUWJI#TJHVJKGLNL#WDHQWSOSLD#JYOOSWLSJN#OGYQNVNWKLVYQJUNLUPU#FUDLGJGYWI#FUSNVSY\YJ#QJYKDQOKYD#IKUVVVHNLKVQHLVVGVLJ#YOJ\TNWYGK#WNYQVNOVOI#IHLNV#+SEQ ID NO: 1, |

35

Example 5: Mouse Immunogenicity Studies Comparing Serotype 3 Ps-$CRM_{197}$ Conjugates Prepared in Aqueous Solution Versus DMSO All animal experiments were performed in strict accordance with the recommendations in the Guide for Care and Use of Laboratory Animals of the National Institutes of Health. The protocol was approved by the Institutional Animal Care and Use Committee (IACUC), MRL, West Point, Pa.

Eight week old female CD1 mice were housed in micro isolator cages (n=10/cage) in the animal facility at MRL, West Point, Pa. Food and water were available ad libitum. Mice (n=10/group) were intramuscularly (IM) immunized with ST3-$CRM_{197}$ conjguates (0.4 μg ST3 polysaccharide), formulated with aluminum phosphate adjuvant (APA) as described in Table 3. Negative control animals received APA alone. Immunizations were performed on days 0, 14 and 28. Blood was collected in serum separator tubes (BD, Franklin Lakes, N.J.) via tail vein on days 6 and 34.

TABLE 3

Mouse study arms comparing serotype 3 Ps-$CRM_{197}$ conjugates prepared in aqueous solution versus DMSO solution.

| Arm # | Arm | Description of Conjugate | Description of Formulation |
|---|---|---|---|
| 1 | APA | Control, no conjugate used | 250 μg/mL APA, 20 mM L-histidine, pH 5.8 and 150 mM NaCl with 0.2% w/v PS-20 |
| 2 | ST3-$CRM_{197}$(aqueous)/APA | Monovalent ST3-$CRM_{197}$ conjugate (Lot #1 in Table 1) prepared by reductive | 0.4 μg ST3-$CRM_{197}$, 250 μg/mL APA, 20 mM L-histidine, pH 5.8 and 150 mM |

TABLE 3-continued

Mouse study arms comparing serotype 3 Ps-CRM$_{197}$ conjugates prepared in aqueous solution versus DMSO solution.

| Arm # | Arm | Description of Conjugate | Description of Formulation |
|---|---|---|---|
| 3 | ST3-CRM$_{197}$(DMSO)/APA | amination in aqueous solution as described in Example 2 Monovalent ST3-CRM$_{197}$ conjugate (Lot #4 in Table 1) prepared by reductive amination in DMSO as described in Example 3 | NaCl with 0.2% w/v PS-20 0.4 µg ST3-CRM$_{197}$, 250 µg/mL APA, 20 mM L-histidine, pH 5.8 and 150 mM NaCl with 0.2% w/v PS-20 |

Electrochemiluminescent (ECL) Immunogenicity Assays

Mouse antibody responses were measured in 96-well multiplexed electrochemiluminescent assays as described previously with slight modifications. See Marchese et al., 2009, Clin Vaccine Immunol 16(3):387-96; Skinner et al., 2011, Vaccine 29(48):8870-6; and Caro-Aguilar et al., 2017 Vaccine 35(6):865-72. Briefly, following test sera incubation for 1 hour on Meso-Scale Discovery plates (Meso Scale Diagnostics, Rockville, Md.) and washing, 25 µl of a 2 µg/ml Sulfo-tag (Meso Scale Diagnostics, Rockville, Md.) labeled goat anti-mouse IgG was added to each well. Plates were incubated for 1 hour at room temperature while shaking and then processed as described previously and read on a MESO Sector 5600.

The ECL titer was calculated as the reciprocal of the linearly interpolated dilution corresponding to the cutoff value (pneumococcal polysaccharide ECL geometric mean signal of pre-determined positive control pooled mouse sera). Interpolation was performed using logarithmic scaling for ECL and the dilution. Titer was then obtained by back-transforming the linearly interpolated dilution. Titers were extrapolated for samples falling outside the studied dilution range of 100 to 1,562,500, based on linear extrapolation (in the log-log scaling) using the intercept and slope of the last 3 ECL data points for the sample curve completely above the cutoff line or using the intercept and slope of the first 2 ECL data points for the sample curve completely below the cutoff line. Titer was then obtained by back-transforming the linearly extrapolated dilution.

Opsonophagocytic Killing Assay (OPA)

Pneumococcal serotype 3 opsonophagocytosis killing assays (OPA) were performed as described previously with slight modifications (Caro-Aguilar et al., 2017 Vaccine 35(6):865-72; and Burton et al., 2006, Clin Vaccine Immunol 13(9):1004-9). Following incubation of the sera, bacteria, complement and HL-60 cells, 10 µl of the opsonophagocytic reaction was transferred to an individual well on a Millipore 96-well filter plate containing 200 µl/well of sterile water. The plate was vacuum filtered and 100 µl of Todd Hewett yeast extract (THYE, Teknova) broth was added. The medium was filtered and the moist plate was placed in a sealed plastic bag overnight at 27° C. Plate filters were then stained with 100 µl/well of a 0.1% Coomassie blue solution (Bio-Rad, Hercules, Calif.). Stain was filtered through the plate, colonies were destained with Coomassie destaining solution (Bio-Rad) and vacuum filtered again until dry. Stained bacterial colonies were counted on a CTL Immunospot reader (Shaker Heights, Ohio). The OPK titer was defined as the reciprocal of the serum dilution with at least 50% killing, compared to the average growth in the complement control (no serum control) wells and was calculated by linearly interpolating between the consecutive dilutions whose signals bracket 50% killing.

Figure 2:
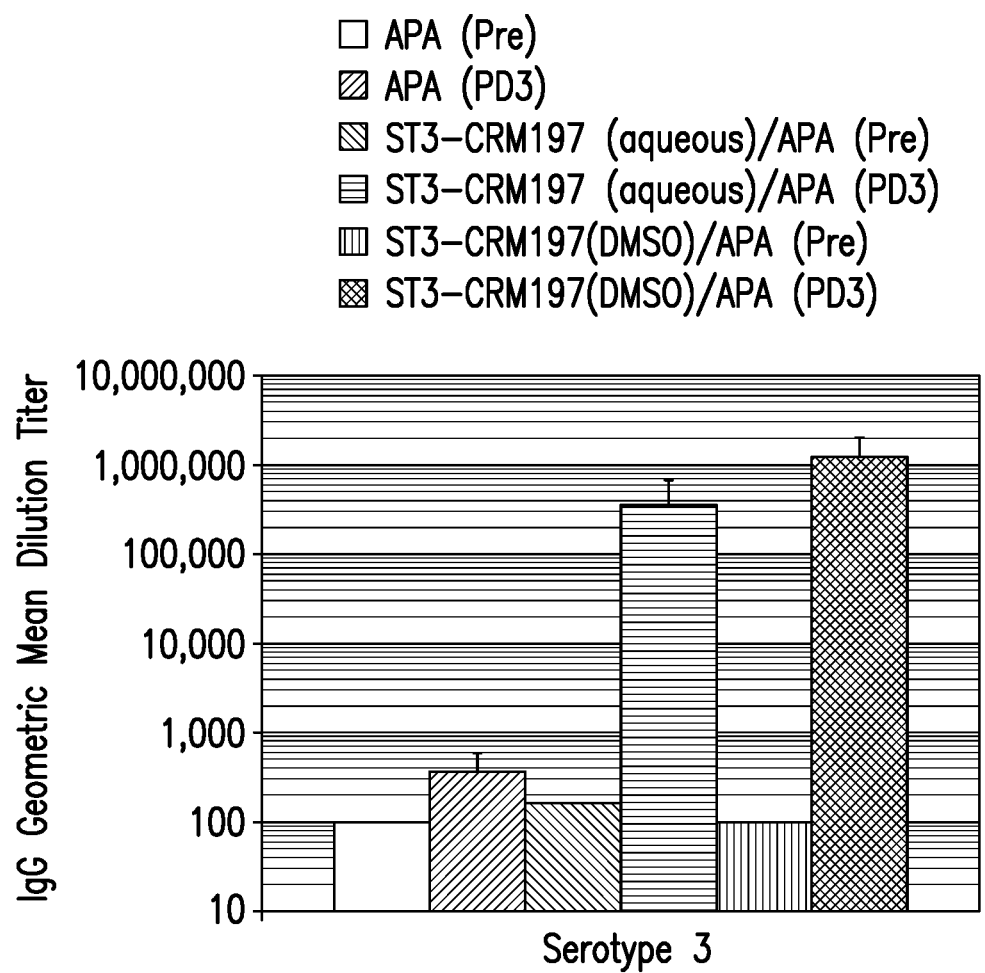
FIG. 2. Electrochemiluminescent (ECL) immunogenicity results from mouse study arms comparing serotype 3 Ps-$CRM_{197}$ conjugates prepared by reductive amination in either aqueous solution or DMSO. Conjugates formulated with aluminum phosphate adjuvant (APA). Pre-vaccination (Pre) and post-dose 3 (PD3) results are shown. Results for APA only control are also shown.
Figure 3:
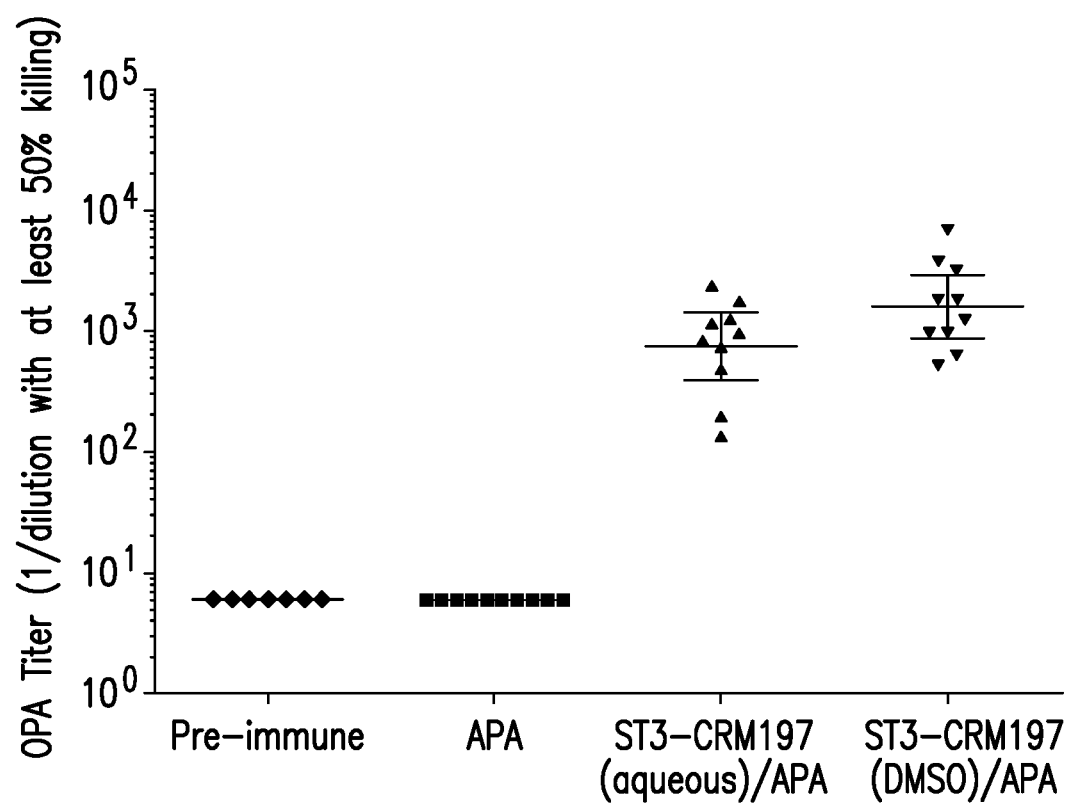
FIG. 3. Post-dose 3 opsophagocytic activity (OPA) results from mouse study arms comparing serotype 3 Ps-$CRM_{197}$ conjugates prepared by reductive amination in either aqueous solution or DMSO. OPA results pre-vaccination (Pre-immune) and for APA only control are also shown.

Results of pre-immunization and post dose 3 are illustrated in FIG. 2 and Table 4 for ECL Immunogenicty, and in FIG. 3 for OPA. Both conjugates prepared by processes using aqueous and DMSO solutions are immunogenic and provide functional killing activities against the bacteria. Interestingly, conjugate prepared by process using DMSO solution gave both higher ECL immunogenicity and OPA responses than conjugate prepared using aqueous solution. The ECL immunogenicity difference is statistically significant. The GMT ratio of Arm 3 relative to Arm 2 is 3.41 (with lower and upper 95% confidence interval of 1.26 and 9.26).

TABLE 4

Post-Dose 3 ECL immunogenicity results of mouse study arms comparing serotype 3 Ps-CRM$_{197}$ conjugates prepared in aqueous solution versus DMSO solution.

| Arm # | Arm | Geometric Mean Titer, GMT | Lower 95% confidence interval | Upper 95% confidence interval |
|---|---|---|---|---|
| 1 | APA | 368 | 227 | 596 |
| 2 | ST3-CRM$_{197}$(aqueous)/ APA | 355,207 | 187,905 | 671,466 |
| 3 | ST3-CRM$_{197}$(DMSO)/ APA | 1,211,654 | 719,297 | 2,041,028 |

Example 6: Adult Human Immunogenicity Studies Comparing Pneumococcal Polysaccharide-Protein Conjugates Prepared with Reductive Amination in Aqueous Solution Versus in DMSO The immunogenicity and safety of two 15-valent pneumococcal conjugate vaccine (PCV15) in healthy Pneumococcal vaccine-naive adults 50 years of age or older is described in this example.

Trial Design

A randomized, multi-site, double-blind trial was carried out to compare the safety, tolerability and immunogenicity of a single dose of 2 different PCV15 formulations (PCV15-A and PCV15-B) and Prevnar 13™ (Pneumococcal 13-valent Conjugate Vaccine [Diphtheria CRM$_{197}$ Protein], Wyeth Pharmaceuticals Inc., a subsidiary of Pfizer Inc., Philadelphia, Pa., USA) in adult subjects 50 years of age or older in good health (any underlying chronic illness must be documented to be in stable condition), to be conducted in conformance with Good Clinical Practices.

A total of 690 healthy Pneumococcal vaccine-naive individuals, 50 years of age or older, were enrolled, and randomized into three different vaccination groups: Prevnar 13™, PCV15-A and PCV15-B with the ratio 1:1:1. Randomization was stratified by age at study entry (50 to 64 years, 65 to 74 years, and ≥75 years).

PCV15 contained 2 μg/0.5 mL dose of each of the following serotypes of Pneumococcal polysaccharide conjugated to $CRM_{197}$ (1, 3, 4, 5, 6A, 7F, 9V, 14, 18C, 19A, 19F, 22F, 23F, 33F), 4 μg/0.5 mL dose of serotype 6B Pneumococcal polysaccharide conjugated to $CRM_{197}$, 125 μg/0.5 mL dose of Aluminum Phosphate Adjuvant, 20 mM L-histidine, 150 mM Sodium Chloride, pH 5.8. PCV15-A was formulated with 0.2% w/v P188. PCV15-B was formulated with 0.1% w/v PS-20.

For PCV15-A, all fifteen polysaccharide serotypes (1, 3, 4, 5, 6A, 6B, 7F, 9V, 14, 18C, 19A, 19F, 22F, 23F, and 33F) were conjugated to $CRM_{197}$ using reductive amination in aqueous solution as described in Example 2. Attributes for some of these conjugates (Conjugate Lot #1 materials) are listed in Table 1.

PCV15-B, serotypes 6A, 6B, 7F, 18C, 19A, 19F, and 23F were conjugated to $CRM_{197}$ using reductive amination in DMSO described in Example 3. Attributes for these conjugates (Conjugate Lot #2 materials) are listed in Table 1. The conjugates for the remaining serotypes (1, 3, 4, 5, 9V, 14, 22F, and 33F) are the same conjugates that were used in PCV15-A.

Both PCV15 formulations had generally comparable safety profiles to Prevnar 13™ based on the cumulative safety evaluation (data not shown). The serotype-specific IgG GMCs and OPA GMTs were measured at Day 30. (OPA results not included).

Results

The IgG Geometric Mean Concentrations (GMCs) and confidence intervals (CI) are summarized in the Table 6. Serotype 6A, 6B, 7F, 18C, 19A, 19F, and 23F conjugates in PCV15-A and PCV15-B were made with different conjugation processes as described above. Consistent with the results shown in Table 4, the immunogenicity responses for each of the serotypes shown in Table 6 was improved when the polysaccharide serotypes were conjugated to $CRM_{197}$ in DMSO. The GMCs for serotypes 18C, 19A, 19F, and 23F in PCV15-B were significantly higher than those in PCV15-A (2-sided alpha=0.05). These data strongly demonstrate the advantage of conjugating in DMSO to improve immunogenicity. This discovery that has not been previously demonstrated for pneumococcal or other conjugate vaccines.

TABLE 6

Summary of IgG antibody responses of PCV15-A, and PCV15-B formulation for serotypes 6A, 6B, 7F, 18C, 19A, 19F, and 23F. Conjugates of these serotypes were made using reductive amination in aqueous solution (PCV15-A) or by reductive amination in DMSO (PCV15-B).

| Serotypes | PCV15-A (N = 231), $GMC^†$ (Day 30) | | PCV15-B (N = 231), $GMC^†$ (Day 30) | | Estimated GMC Ratio$^†$ [PCV15-B/ PCV15-A] (95% CI)$^†$ |
|---|---|---|---|---|---|
| | n | Estimated Response | n | Estimated Response | |
| 6A | 217 | 3.74 | 217 | 4.93 | 1.32 (0.96, 1.81) |
| 6B | 217 | 3.69 | 217 | 4.95 | 1.34 (0.98, 1.85) |
| 7F | 217 | 4.09 | 217 | 4.53 | 1.11 (0.86, 1.43) |
| 18C | 217 | 6.61 | 217 | 10.99 | 1.66 (1.27, 2.18) |
| 19A | 217 | 8.77 | 217 | 13.83 | 1.58 (1.23, 2.02) |
| 19F | 217 | 4.11 | 217 | 6.80 | 1.66 (1.26, 2.17) |
| 23F | 217 | 3.92 | 217 | 5.53 | 1.41 (1.04, 1.91) |

$^†$Estimated GMCs, GMC ratio, and 95% CI are obtained from a cLDA model.

N = Number of subjects randomized and vaccinated.

n = Number of subjects with Day 30 postvaccination serology results contributing to the analysis.

GMC = Geometric Mean Concentration.

CI = Confidence interval

What is claimed is:

1. An immunogenic composition consisting essentially of polysaccharide from S. pneumoniae serotypes 1, 3, 4, 5, 6A, 6B, 7F, 9V, 14, 18C, 19A, 19F, 22F, 23F and 33F each conjugated to a carrier protein, wherein the conjugation reaction for S. pneumoniae serotypes 6A, 6B, 7F, 18C, 19A, 19F, and 23F is in an aprotic solvent and the conjugation reaction for S. pneumoniae serotypes 1, 3, 4, 5, 9V, 14, 22F and 33F is in an aqueous solvent.

2. The immunogenic composition of claim 1, wherein the conjugation reaction is reductive amination.

3. The immunogenic composition of claim 1, wherein the carrier protein is $CRM_{197}$.

4. The immunogenic composition of claim 1, wherein the aprotic solvent is dimethylsulfoxide (DMSO).

5. The immunogenic composition of claim 1, further comprising about 0.2% w/v Polysorbate 20.

6. An immunogenic composition consisting essentially of polysaccharide from S. pneumoniae serotypes 1, 3, 4, 5, 6A, 6B, 7F, 9V, 14, 18C, 19A, 19F, 22F, 23F and 33F each conjugated to $CRM_{197}$; wherein the conjugation reaction for S. pneumoniae serotypes 6A, 6B, 7F, 18C, 19A, 19F, and 23F is in an aprotic solvent, wherein the aprotic solvent is DMSO; and the conjugation reaction for S. pneumoniae serotypes 1, 3, 4, 5, 9V, 14, 22F and 33F is in an aqueous solvent.

7. The immunogenic composition of claim 6, further comprising about 0.2% w/v Polysorbate 20.

8. An immunogenic composition consisting of polysaccharide from S. pneumoniae serotypes 1, 3, 4, 5, 6A, 6B, 7F, 9V, 14, 18C, 19A, 19F, 22F, 23F and 33F each conjugated to a carrier protein, wherein the conjugation reaction for S. pneumoniae serotypes 6A, 6B, 7F, 18C, 19A, 19F, and 23F is in an aprotic solvent and the conjugation reaction for S. pneumoniae serotypes 1, 3, 4, 5, 9V, 14, 22F and 33F is in an aqueous solvent.

9. The immunogenic composition of claim 8, wherein the conjugation reaction is reductive amination.

10. The immunogenic composition of claim 8, wherein the carrier protein is $CRM_{197}$.

11. The immunogenic composition of claim 8, wherein the aprotic solvent is dimethylsulfoxide (DMSO).

12. The immunogenic composition of claim 8, further comprising about 0.2% w/v Polysorbate 20.

13. An immunogenic composition consisting of polysaccharide from S. pneumoniae serotypes 1, 3, 4, 5, 6A, 6B, 7F, 9V, 14, 18C, 19A, 19F, 22F, 23F and 33F each conjugated to $CRM_{197}$; wherein the conjugation reaction for S. pneumoniae serotypes 6A, 6B, 7F, 18C, 19A, 19F, and 23F is in an aprotic solvent, wherein the aprotic solvent is DMSO; and the conjugation reaction for S. pneumoniae serotypes 1, 3, 4, 5, 9V, 14, 22F and 33F is in an aqueous solvent.

14. The immunogenic composition of claim 13, further comprising about 0.2% w/v Polysorbate 20.

* * * * *

SEQUENCE LISTING

<160> NUMBER OF SEQ ID NOS: 1

<210> SEQ ID NO 1
<211> LENGTH: 535
<212> TYPE: PRT
<213> ORGANISM: Artificial Sequence
<220> FEATURE:
<223> OTHER INFORMATION: CRM197 (detoxified variant of diphtheria toxin)

<400> SEQUENCE: 1

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95
```

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
            130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
            210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
            290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
            370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
            450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

```
Gly Tyr Gln Lys Thr Val Asp His Thr Lys Val Asn Ser Lys Leu Ser
        515                 520                 525
Leu Phe Phe Glu Ile Lys Ser
    530             535
```